(12) United States Patent
Sur

(10) Patent No.: US 11,439,189 B2
(45) Date of Patent: Sep. 13, 2022

(54) MESH NETWORK CHARGING FOR AEROSOL DELIVERY DEVICES

(71) Applicant: RAI STRATEGIC HOLDINGS, INC., Winston-Salem, NC (US)

(72) Inventor: Rajesh Sur, Winston-Salem, NC (US)

(73) Assignee: RAI Strategic Holdings, Inc., Winston-Salem, NC (US)

(*) Notice: Subject to any disclaimer, the term of this patent is extended or adjusted under 35 U.S.C. 154(b) by 331 days.

(21) Appl. No.: 16/860,670

(22) Filed: Apr. 28, 2020

(65) Prior Publication Data

US 2021/0329977 A1 Oct. 28, 2021

(51) Int. Cl.
| | | |
|---|---|---|
| *A24F 40/90* | (2020.01) | |
| *A24F 40/51* | (2020.01) | |
| *A24F 40/60* | (2020.01) | |
| *H02J 7/02* | (2016.01) | |
| *H02J 50/00* | (2016.01) | |
| *H02J 50/20* | (2016.01) | |
| *A61M 15/06* | (2006.01) | |

(52) U.S. Cl.
CPC .............. *A24F 40/90* (2020.01); *A24F 40/51* (2020.01); *A24F 40/60* (2020.01); *A61M 15/06* (2013.01); *H02J 7/02* (2013.01); *H02J 50/001* (2020.01); *H02J 50/20* (2016.02)

(58) Field of Classification Search
CPC .......... A24F 40/90; A24F 40/51; A24F 40/60; A24F 40/10; A24F 40/20; A24F 40/465; A61M 15/06; A61M 2016/0018; A61M 2016/0039; A61M 2205/123; A61M 2205/127; A61M 2205/3592; A61M 2205/50; A61M 2205/587; A61M 2205/8206; A61M 2205/8243; A61M 2205/8256; A61M 11/042; H02J 7/02; H02J 50/001; H02J 50/20
See application file for complete search history.

(56) References Cited

U.S. PATENT DOCUMENTS

| | | |
|---|---|---|
| 2,057,353 A | 10/1936 | Whittemore, Jr. |
| 2,104,266 A | 1/1938 | McCormick |
| 3,200,819 A | 8/1965 | Gilbert |
| 4,922,901 A | 5/1990 | Brooks et al. |
| 5,060,671 A | 10/1991 | Counts et al. |

(Continued)

FOREIGN PATENT DOCUMENTS

| | | |
|---|---|---|
| CN | 1541577 | 11/2004 |
| CN | 2719043 | 8/2005 |

(Continued)

*Primary Examiner* — Daniel Cavallari
(74) *Attorney, Agent, or Firm* — Womble Bond Dickinson (US) LLP

(57) ABSTRACT

Power harvesting and radio frequency (RF) transmission circuitry for an aerosol delivery device is provided. The aerosol delivery device includes power harvesting circuitry configured to receive RF energy from an external RF source and harvest power from the RF energy to charge a rechargeable power source and power transmission circuity operatively coupled to the power source and configured to convert electrical energy drawn from the power source to RF energy and transmit the RF energy. RF energy can thus be transmitted through a network of aerosol delivery devices to extend the range of an RF energy source.

25 Claims, 15 Drawing Sheets

(56) References Cited

U.S. PATENT DOCUMENTS

| | | |
|---|---|---|
| 5,093,894 A | 3/1992 | Deevi et al. |
| 5,261,424 A | 11/1993 | Sprinkel, Jr. |
| 5,388,574 A | 2/1995 | Ingebrethsen et al. |
| 5,530,225 A | 6/1996 | Hajaligol |
| 5,687,746 A | 11/1997 | Rose et al. |
| 5,726,421 A | 3/1998 | Fleischhauer et al. |
| 5,865,185 A | 2/1999 | Collins et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Teny et al. |
| 8,365,742 B2 | 2/2013 | Hon |
| 8,499,766 B1 | 8/2013 | Newton |
| 2005/0016550 A1 | 1/2005 | Katase |
| 2006/0196518 A1 | 9/2006 | Hon |
| 2008/0092912 A1 | 4/2008 | Robinson et al. |
| 2009/0095311 A1 | 4/2009 | Hon |
| 2009/0126745 A1 | 5/2009 | Hon |
| 2009/0188490 A1 | 7/2009 | Hon |
| 2009/0272379 A1 | 11/2009 | Thorens et al. |
| 2011/0094523 A1 | 4/2011 | Thorens et al. |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2012/0111347 A1 | 5/2012 | Hon |
| 2012/0260927 A1 | 10/2012 | Liu |
| 2012/0279512 A1 | 11/2012 | Hon |
| 2013/0037041 A1 | 2/2013 | Worm et al. |
| 2013/0056013 A1 | 3/2013 | Terry et al. |
| 2013/0306084 A1 | 11/2013 | Flick |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |

FOREIGN PATENT DOCUMENTS

| | | | |
|---|---|---|---|
| CN | 201379072 | 1/2010 | |
| EP | 0 295 122 | 12/1988 | |
| EP | 0 845 220 | 6/1998 | |
| EP | 1 618 803 | 1/2006 | |
| EP | 3177351 B1 * | 10/2018 | ........... A24B 15/167 |
| GB | 2469850 | 11/2010 | |
| WO | WO 2003/034847 | 5/2003 | |
| WO | WO 2004/080216 | 9/2004 | |
| WO | WO 2005/099494 | 10/2005 | |
| WO | WO 2007/131449 | 11/2007 | |

* cited by examiner

MESH NETWORK CHARGING FOR AEROSOL DELIVERY DEVICES

TECHNOLOGICAL FIELD

The present disclosure relates to aerosol delivery devices, and more particularly to aerosol delivery devices that may harvest electrical energy from radio frequency (RF) transmissions. The harvested electrical energy may be used to power an aerosol production component and other components in the aerosol delivery device.

BACKGROUND

Many smoking articles have been proposed through the years as improvements upon, or alternatives to, smoking products based upon combusting tobacco. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. 6,164,287 to White; U.S. Pat No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. Pub. No. 2009/0095311 to Hon; U.S. Pat. Pub. Nos. 2006/0196518, 2009/0126745, and 2009/0188490 to Hon; U.S. Pat. Pub. No. 2009/0272379 to Thorens et al.; U.S. Pat. Pub. Nos. 2009/0260641 and 2009/0260642 to Monsees et al.; U.S. Pat. Pub. Nos. 2008/0149118 and 2010/0024834 to Oglesby et al.; U.S. Pat. Pub. No. 2010/0307518 to Wang; and WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™, HENDU™ JET™, MAXXQ™ PINK™ and PITBULL™ by SMOKE STIK®, HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; MISTIC MENTHOL product by Mistic Ecigs; the VYPE product by CN Creative Ltd; IQOS™ by Philip Morris International; GLO™ by British American Tobacco; MARK TEN products by Nu Mark LLC; and the JUUL product by Juul Labs, Inc. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™.

It would be desirable to provide aerosol delivery devices with functionality for converting radio frequency energy to direct current power, and for aerosol delivery devices to interact with each other to extend the effective range of a radio frequency transmission used to power one or more aerosol delivery devices.

BRIEF SUMMARY

The present disclosure relates to aerosol delivery devices, methods of forming such devices, and elements of such devices. Some example implementations involve one or more aerosol delivery devices that are configured to receive radio-frequency (RF) energy from an external RF source and harvest power from the RF energy to charge a rechargeable power source. In some such example implementations, the one or more aerosol delivery devices are also configured to convert electrical energy drawn from their respective power sources into RF energy and transmit the RF energy. As such, some example implementations involve the formation of a mesh network by multiple aerosol delivery devices, and the use of that network to transmit RF energy to charge aerosol delivery devices.

The present disclosure thus includes, without limitation, the following example implementations.

In some example implementations, an apparatus embodied as an aerosol delivery device is provided. In such example implementations, the aerosol delivery device may comprise a housing structured to retain an aerosol precursor composition; an aerosol production component configured to produce an aerosol from the aerosol precursor composition; power harvesting circuitry configured to receive radio-frequency (RF) energy from an external RF source and harvest power from the RF energy to charge a rechargeable power source; and power transmission circuity operatively coupled to the power source and configured to convert electrical energy drawn from the power source to RF energy and transmit the RF energy.

In some example implementations of the apparatus of any preceding or any subsequent example implementation, or any combination thereof, the power harvesting circuitry is further configured to receive RF energy from a plurality of RF sources, the plurality of RF sources disposed within a mesh network architecture.

In some example implementations of the apparatus of any preceding or any subsequent example implementation, or any combination thereof, the power transmission circuitry is further configured to transmit RF energy to a remote aerosol delivery device disposed within a mesh network architecture.

In some example implementations of the apparatus of any preceding or any subsequent example implementation, or any combination thereof, the aerosol delivery device further comprises an antenna operatively coupled to the power harvesting circuitry and the power transmission circuitry, the antenna configured to receive and transmit RF energy.

In some example implementations of the apparatus of any preceding or any subsequent example implementation, or any combination thereof, the aerosol delivery device further comprises processing circuitry contained within the housing, the processing circuitry configured to selectively activate and deactivate the power harvesting circuitry and selectively activate and deactivate the power transmission circuitry.

In some example implementations of the apparatus of any preceding or any subsequent example implementation, or any combination thereof, the processing circuitry is configured to selectively activate and deactivate the power harvesting circuitry and the power transmission circuitry based on a charging status of the rechargeable power source.

In some example implementations of the apparatus of any preceding or any subsequent example implementation, or any combination thereof, the processing circuitry is configured to selectively activate and deactivate the power harvesting circuitry and the power transmission circuitry based at least in part on a distance between the aerosol delivery device and a remote aerosol delivery device.

In some example implementations of the apparatus of any preceding or any subsequent example implementation, or any combination thereof, the processing circuitry is configured to selectively deactivate the power harvesting circuitry in response to a user input.

In some example implementations of the apparatus of any preceding or any subsequent example implementation, or any combination thereof, the processing circuitry is configured to selectively deactivate the power harvesting circuitry in response to a flow of air through at least a portion of the housing.

In some example implementations of the apparatus of any preceding or any subsequent example implementation, or any combination thereof, the processing circuitry is configured to selectively deactivate the power transmission circuitry in response to a user input.

In some example implementations of the apparatus of any preceding or any subsequent example implementation, or any combination thereof, the processing circuitry is configured to selectively deactivate the power transmission circuitry in response to a flow of air through at least a portion of the housing.

In some example implementations, an apparatus is provided in the form of a control body coupled or coupleable with a cartridge to form an aerosol delivery device, the cartridge containing an aerosol precursor composition and an aerosol production component configured to produce an aerosol from the aerosol precursor composition, the control body comprising power harvesting circuitry configured to receive radio-frequency (RF) energy from an external RF source and harvest power from the RF energy to charge a rechargeable power source and power transmission circuity operatively coupled to the power source and configured to convert electrical energy drawn from the power source to RF energy and transmit the RF energy.

In some example implementations of the control body of any preceding or any subsequent example implementation, or any combination thereof, the power harvesting circuitry is further configured to receive RF energy from a plurality of RF sources, the plurality of RF sources disposed within a mesh network architecture.

In some example implementations of the control body of any preceding or any subsequent example implementation, or any combination thereof, the power transmission circuitry is further configured to transmit RF energy to a remote aerosol delivery device disposed within a mesh network architecture.

In some example implementations of the control body of any preceding or any subsequent example implementation, or any combination thereof, the control body further comprises an antenna operatively coupled to the power harvesting circuitry and the power transmission circuitry, the antenna configured to receive and transmit RF energy.

In some example implementations of the control body of any preceding or any subsequent example implementation, or any combination thereof, the control body further comprises processing circuitry configured to selectively activate and deactivate the power harvesting circuitry and selectively activate and deactivate the power transmission circuitry.

In some example implementations of the control body of any preceding or any subsequent example implementation, or any combination thereof, the processing circuitry is configured to selectively activate and deactivate the power harvesting circuitry and the power transmission circuitry based on a charging status of the rechargeable power source.

In some example implementations of the control body of any preceding or any subsequent example implementation, or any combination thereof, the processing circuitry is configured to selectively activate and deactivate the power harvesting circuitry and the power transmission circuitry based at least in part on a distance between the aerosol delivery device and a remote aerosol delivery device.

In some example implementations of the control body of any preceding or any subsequent example implementation, or any combination thereof, the processing circuitry is configured to selectively deactivate the power harvesting circuitry in response to a user input.

In some example implementations of the control body of any preceding or any subsequent example implementation, or any combination thereof, the processing circuitry is configured to selectively deactivate the power harvesting circuitry in response to a flow of air through at least a portion of the housing.

In some example implementations of the control body of any preceding or any subsequent example implementation, or any combination thereof, the processing circuitry is configured to selectively deactivate the power transmission circuitry in response to a user input.

In some example implementations of the control body of any preceding or any subsequent example implementation, or any combination thereof, the processing circuitry is configured to selectively deactivate the power transmission circuitry in response to a flow of air through at least a portion of the housing.

In some example implementations, a system for operating aerosol delivery devices is provided, system comprising: a plurality of aerosol delivery devices comprising respective power harvesting circuitry and respective power transmission circuitry, wherein the respective the power harvesting circuitry of an aerosol delivery device in the plurality of aerosol delivery devices configured to receive radio frequency (RF) energy from the respective power transmission circuitry of another aerosol delivery device in the plurality of aerosol delivery devices that is configured to transmit the RF energy.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

Figure 16:
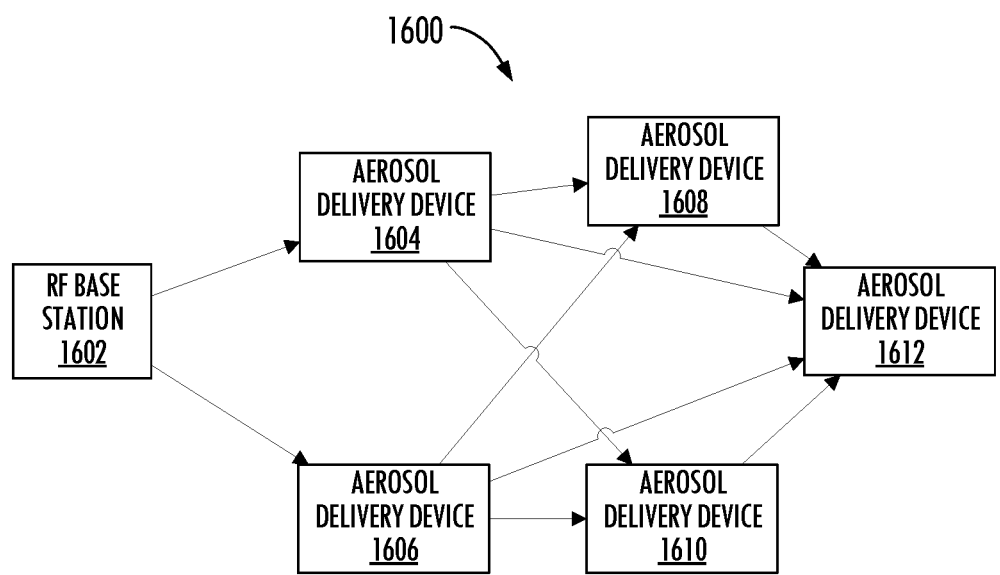
Figure 17:
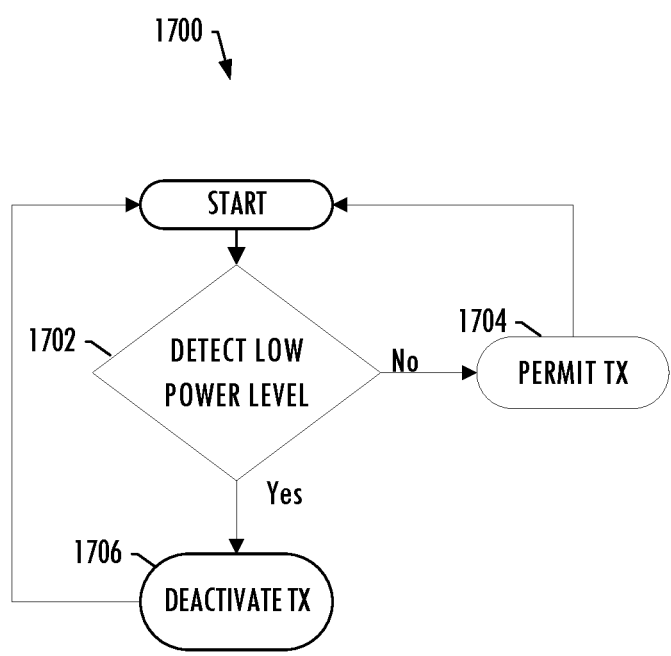
Figure 18:
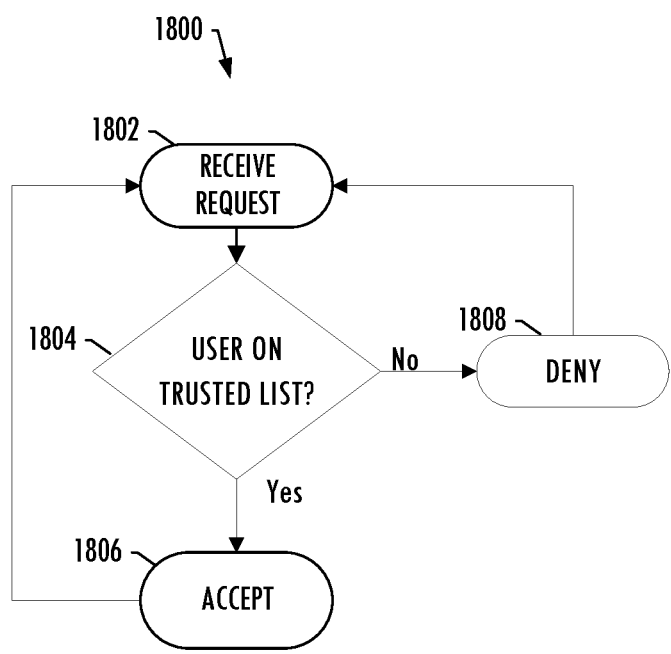
Figure 19:
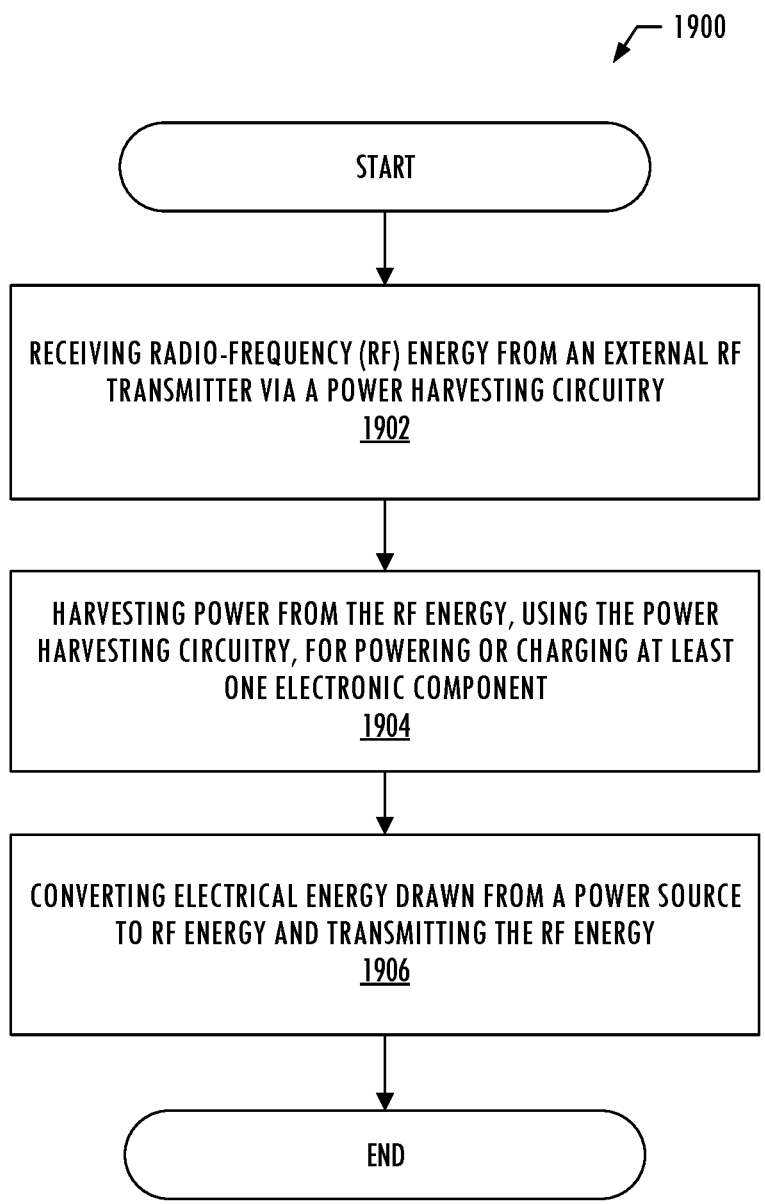

FIGS. 10, 11, 12, 13, 14, and 15 illustrate various elements of the control body, according to various example implementations;

FIG. 16 illustrates an example mesh network, according to various example implementations;

FIG. 17 illustrates various operations in a method for controlling an aerosol delivery device, according to an example implementation;

FIG. 18 is a flowchart illustrating a decision flow that may be used by a control component according to an example implementation; and FIG. 19 is a flowchart illustrating another decision flow that may be used by a control component according to an example implementation.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Some aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that component for inhalation of aerosol produced by that component, take or draw puffs at selected intervals of time, and the like.

While the systems are generally described herein in terms of implementations associated with aerosol delivery devices such as so-called "e-cigarettes," "tobacco heating products" and the like, it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer housing, which may be referred to as a body or shell. The overall design of the housing can vary, and the format or configuration of the housing that can define the overall size and shape of the aerosol delivery device can vary. Typically, an elongated body resembling the shape of a cigarette or cigar can be formed from a single, unitary housing or the elongated housing can be formed of two or more separable bodies. For example, an aerosol delivery device can comprise an elongated housing that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery, rechargeable supercapacitor, solid-state battery (SSB), thin-film SSB, lithium-ion or hybrid lithium-ion supercapacitor, and various electronics for controlling the operation of that article), and at the other end and removably coupleable thereto, an outer body or shell containing a disposable portion (e.g., a disposable flavor-containing cartridge). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices. It will be appreciated that alternative non-tubular housing form factors can also be used, including, for example, device housings having a shape and size generally approximating a pack of cigarettes and form factors such as used on the GLO™ by British American Tobacco and IQOS™ by Philip Morris International, Inc.

As will be discussed in more detail below, aerosol delivery devices of the present disclosure comprise some combination of a power source (i.e., an electrical power source), at least one control component (e.g., means for actuating, controlling, regulating and ceasing power for heat generation, such as by controlling electrical current flow from the power source to other components of the aerosol delivery device), a heating element (e.g., an electrical resistance heating element or other component and/or an inductive coil or other associated components and/or one or more radiant heating elements), and an aerosol precursor composition (e.g., a solid tobacco material, a semi-solid tobacco material, or a liquid aerosol precursor composition) capable of yielding an aerosol upon application of sufficient heat, and a mouth end region or tip to allow drawing upon the aerosol delivery device for aerosol inhalation (e.g., a defined airflow path through the article such that aerosol generated can be withdrawn therefrom upon draw). In some implementations, the power source includes a single battery or a single battery cell. The power source can power the heating element that is configured to convert electricity to heat and thereby vaporize components of an aerosol precursor composition.

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element may be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery, supercapacitor, SSB or other power source to provide current flow sufficient to provide various functionalities to the aerosol delivery device, such as powering of a heating element, powering of control systems, powering of indicators, and the like. The power source can take on various implementations. Preferably, the power source is able to deliver sufficient power to rapidly activate the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

As described hereinafter, the present disclosure relates to aerosol delivery devices. Aerosol delivery devices may be configured to heat an aerosol precursor composition (sometimes referred to as an inhalable substance medium) to produce an aerosol (an inhalable substance). The aerosol precursor composition may comprise one or more of a solid tobacco material, a semi-solid tobacco material, or a liquid aerosol precursor composition. In some implementations, the aerosol delivery devices may be configured to heat and produce an aerosol from a fluid aerosol precursor composition (e.g., a liquid aerosol precursor composition). Such aerosol delivery devices may include so-called electronic cigarettes. In other implementations, the aerosol delivery devices may comprise heat-not-burn devices.

Liquid aerosol precursor composition, also referred to as a vapor precursor composition or "e-liquid," is particularly useful for electronic cigarettes and no-heat-no-burn devices, as well as other devices that atomize or otherwise aerosolize a liquid to generate an inhalable aerosol. Liquid aerosol precursor composition may comprise a variety of components including, by way of example, a polyhydric alcohol (e.g., glycerin, propylene glycol, or a mixture thereof), nicotine, tobacco, tobacco extract, and/or flavorants. In some examples, the aerosol precursor composition comprises glycerin and nicotine.

Some liquid aerosol precursor compositions that may be used in conjunction with various implementations may include one or more acids such as levulinic acid, succinic acid, lactic acid, pyruvic acid, benzoic acid, fumaric acid, combinations thereof, and the like. Inclusion of an acid(s) in liquid aerosol precursor compositions including nicotine may provide a protonated liquid aerosol precursor composition, including nicotine in salt form. Representative types of liquid aerosol precursor components and formulations are set forth and characterized in U.S. Pat. No. 7,726,320 to Robinson et al., U.S. Pat. No. 9,254,002 to Chong et al., and U.S. Pat. App. Pub. Nos. 2013/0008457 to Zheng et al., 2015/0020823 to Lipowicz et al., and 2015/0020830 to Koller, as well as PCT Pat. App. Pub. No. WO 2014/182736 to Bowen et al., and U.S. Pat. No. 8,881,737 to Collett et al., the disclosures of which are incorporated herein by reference. Other aerosol precursors that may be employed include the aerosol precursors that have been incorporated in any of a number of the representative products identified above. Also desirable are the so-called "smoke juices" for electronic cigarettes that have been available from Johnson Creek Enterprises LLC. Still further example aerosol precursor compositions are sold under the brand names BLACK NOTE, COSMIC FOG THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al., U.S. Pat. No. 5,178,878 to Wehling et al., U.S. Pat. No. 5,223,264 to Wehling et al., U.S. Pat. No. 6,974,590 to Pather et al., U.S. Pat. No. 7,381,667 to Bergquist et al., U.S. Pat. No. 8,424,541 to Crawford et al, U.S. Pat. No. 8,627,828 to Strickland et al., and U.S. Pat. No. 9,307,787 to Sun et al., as well as U.S. Pat. App. Pub. Nos. 2010/0018539 to Brinkley et al., and PCT Pat. App. Pub. No. WO 97/06786 to Johnson et al., all of which are incorporated by reference herein.

The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD).

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

In other implementations, the aerosol delivery devices may comprise heat-not-burn devices, configured to heat a solid aerosol precursor composition (e.g., an extruded tobacco rod) or a semi-solid aerosol precursor composition (e.g., a glycerin-loaded tobacco paste). The aerosol precursor composition may comprise tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Representative types of solid and semi-solid aerosol precursor compositions and formulations are disclosed in U.S. Pat. No. 8,424,538 to Thomas et al., U.S. Pat. No. 8,464,726 to Sebastian et al., U.S. Pat. App. Pub. No. 2015/0083150 to Conner et al., U.S. Pat. App. Pub. No. 2015/0157052 to Ademe et al., and U.S. Pat. App. Pub. No. 2017/0000188 to Nordskog et al., all of which are incorporated by reference herein. Further representative types of solid and semi-solid aerosol precursor compositions and arrangements include those found in the NEOSTIKS™ consumable aerosol source members for the GLO™ product by British American Tobacco and in the HEETS™ consumable aerosol source members for the IQOS™ product by Philip Morris International, Inc.

In various implementations, the inhalable substance specifically may be a tobacco component or a tobacco-derived material (i.e., a material that is found naturally in tobacco that may be isolated directly from the tobacco or synthetically prepared). For example, the aerosol precursor composition may comprise tobacco extracts or fractions thereof combined with an inert substrate. The aerosol precursor composition may further comprise unburned tobacco or a composition containing unburned tobacco that, when heated to a temperature below its combustion temperature, releases an inhalable substance. In some implementations, the aerosol precursor composition may comprise tobacco condensates or fractions thereof (i.e., condensed components of the smoke produced by the combustion of tobacco, leaving flavors and, possibly, nicotine).

Tobacco materials useful in the present disclosure can vary and may include, for example, flue-cured tobacco, burley tobacco, Oriental tobacco or Maryland tobacco, dark tobacco, dark-fired tobacco and *Rustica* tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al., U.S. Pat. No. 4,924,888 to Perfetti et al., U.S. Pat. No. 5,056,537 to Brown et al., U.S. Pat. No. 5,159,942 to Brinkley et al., U.S. Pat. No. 5,220,930 to Gentry, U.S. Pat. No. 5,360,023 to Blakley et al., U.S. Pat. No. 6,701,936 to Shafer et al., U.S. Pat. No. 7,011,096 to Li et al., and U.S. Pat. No. 7,017,585 to Li et al., U.S. Pat. No. 7,025,066 to Lawson et al., U.S. Pat. App. Pub. No. 2004/0255965 to Perfetti et al., PCT Pat. App. Pub. No. WO 02/37990 to Bereman, and Bombick et al., Fund. Appl. Toxicol., 39, p. 11-17 (1997), which are incorporated herein by reference. Further example tobacco compositions that may be useful in a smoking device, including according to the present disclosure, are disclosed in U.S. Pat. No. 7,726,320 to Robinson et al., which is incorporated herein by reference.

Still further, the aerosol precursor composition may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the aerosol precursor composition may comprise a blend of flavorful and aromatic tobaccos in cut filler form. In another aspect, the aerosol precursor composition may comprise a reconstituted tobacco material, such as described in U.S. Pat. No. 4,807,809 to Pryor et al., U.S. Pat. No. 4,889,143 to Pryor et al. and U.S. Pat. No. 5,025,814 to Raker, the disclosures of which are incorporated herein by reference. For further information regarding suitable aerosol precursor composition, see U.S. patent application Ser. No. 15/916,834 to Sur et al., filed Mar. 9, 2018, which is incorporated herein by reference.

Regardless of the type of aerosol precursor composition heated, aerosol delivery devices may include a heating element configured to heat the aerosol precursor composition. In some implementations, the heating element is an induction heater. Such heaters often comprise an induction transmitter and an induction receiver. The induction transmitter may include a coil configured to create an oscillating magnetic field (e.g., a magnetic field that varies periodically with time) when alternating current is directed through it. The induction receiver may be at least partially located or received within the induction transmitter and may include a conductive material (e.g., ferromagnetic material or an aluminum coated material). By directing alternating current through the induction transmitter, eddy currents may be generated in the induction receiver via induction. The eddy currents flowing through the resistance of the material defining the induction receiver may heat it by Joule heating (i.e., through the Joule effect). The induction receiver, which may define an atomizer, may be wirelessly heated to form an aerosol from an aerosol precursor composition positioned in proximity to the induction receiver. Various implementations of an aerosol delivery device with an induction heater are described in U.S. Pat. App. Pub. No. 2017/0127722 to Davis et al., U.S. Pat. App. Pub. No. 2017/0202266 to Sur et al., U.S. patent application Ser. No. 15/352,153 to Sur et al., filed Nov. 15, 2016, U.S. patent application Ser. No. 15/799,365 to Sebastian et al., filed Oct. 31, 2017, and U.S. patent application Ser. No. 15/836,086 to Sur, all of which are incorporated by reference herein.

In other implementations including those described more particularly herein, the heating element is a conductive heater such as in the case of electrical resistance heater. These heaters may be configured to produce heat when an electrical current is directed through it. In various implementations, a conductive heater may be provided in a variety forms, such as in the form of a foil, a foam, a plate, discs, spirals, fibers, wires, films, yarns, strips, ribbons or cylinders. Such heaters often include a metal material and are configured to produce heat as a result of the electrical resistance associated with passing an electrical current through it. Such resistive heaters may be positioned in proximity to and heat an aerosol precursor composition to produce an aerosol. A variety of conductive substrates that may be usable with the present disclosure are described in the above-cited U.S. Pat. App. Pub. No. 2013/0255702 to Griffith et al. Other examples of suitable heaters are described in U.S. Pat. No. 9,491,974 to DePiano et al., which is incorporated by reference herein.

In some implementations aerosol delivery devices may include a control body and a cartridge in the case of so-called electronic cigarettes, or a control body and an aerosol source member in the case of heat-not-burn devices. In the case of either electronic cigarettes or heat-not-burn devices, the control body may be reusable, whereas the cartridge/aerosol source member may be configured for a limited number of uses and/or configured to be disposable. The cartridge/aerosol source member may include the aerosol precursor composition. In order to heat the aerosol precursor composition, the heating element may be positioned in contact with or proximate the aerosol precursor composition, such as across the control body and cartridge, or in the control body in which the aerosol source member may be positioned. The control body may include a power source, which may be rechargeable or replaceable, and thereby the control body may be reused with multiple cartridges/aerosol source members.

The control body may also include means to activate the aerosol delivery device such as a pushbutton, touch-sensitive surface or the like for manual control of the device. Additionally or alternatively, the control body may include a flow sensor to detect when a user draws on the cartridge/aerosol source member to thereby activate the aerosol delivery device.

In various implementations, the aerosol delivery device according to the present disclosure may have a variety of overall shapes, including, but not limited to an overall shape that may be defined as being substantially rod-like, rod-shaped or substantially tubular shaped or substantially cylindrically shaped. In the implementations shown in and described with reference to the accompanying figures, the aerosol delivery device has a substantially round cross-section; however, other cross-sectional shapes (e.g., oval, square, rectangle, triangle, etc.) also are encompassed by the present disclosure. Such language that is descriptive of the physical shape of the article may also be applied to the individual components thereof, including the control body and the cartridge/aerosol source member. In other implementations, the control body may take another handheld shape, such as a small box shape.

In more specific implementations, one or both of the control body and the cartridge/aerosol source member may be referred to as being disposable or as being reusable. For example, the control body may have a power source such as a replaceable battery or a rechargeable battery, SSB, thin-film SSB, rechargeable supercapacitor, lithium-ion or hybrid lithium-ion supercapacitor, or the like. One example of a power source is a TKI-1550 rechargeable lithium-ion battery produced by Tadiran Batteries GmbH of Germany. In another implementation, a useful power source may be a N50-AAA CADNICA nickel-cadmium cell produced by Sanyo Electric Company, Ltd., of Japan. In other implementations, a plurality of such batteries, for example providing 1.2-volts each, may be connected in series.

In some examples, then, the power source may be connected to and thereby combined with any type of recharging technology. Examples of suitable chargers include chargers that simply supply constant or pulsed direct current (DC) power to the power source, fast chargers that add control circuitry, three-stage chargers, induction-powered chargers, smart chargers, motion-powered chargers, pulsed chargers, solar chargers, USB-based chargers and the like. In some examples, the charger includes a power adapter and any suitable charge circuitry. In other examples, the charger includes the power adapter and the control body is equipped with charge circuitry. In these other examples, the charger may at times be simply referred to as a power adapter.

The control body may include any of a number of different terminals, electrical connectors or the like to connect to a suitable charger, and in some examples, to connect to other peripherals for communication. More specific suitable examples include direct current (DC) connectors such as cylindrical connectors, cigarette lighter connectors and USB connectors including those specified by USB 1.x (e.g., Type A, Type B), USB 2.0 and its updates and additions (e.g., Mini A, Mini B, Mini AB, Micro A, Micro B, Micro AB) and USB 3.x (e.g., Type A, Type B, Micro B, Micro AB, Type C), proprietary connectors such as Apple's Lightning connector, and the like. The control body may directly connect with the charger or other peripheral, or the two may connect via an appropriate cable that also has suitable connectors. In examples in which the two are connected by cable, the control body and charger or other peripheral may have the same or different type of connector with the cable having the one type of connector or both types of connectors.

In examples involving wireless charging, the aerosol delivery device may be equipped with a wireless charging technology, such as an inductive charging technology, radio charging technology, or resonance charging technology. For example, in implementations in which the aerosol delivery device is configured to implement an inductive wireless charging technology, the aerosol delivery device may include an induction receiver to connect with a wireless charger, charging pad or the like that includes an induction transmitter and uses inductive wireless charging (including for example, wireless charging according to the Qi wireless charging standard from the Wireless Power Consortium (WPC)). Or the power source may be recharged from a wireless radio frequency (RF) based charger. An example of an inductive wireless charging system is described in U.S. Pat. App. Pub. No. 2017/0112196 to Sur et al., which is incorporated herein by reference in its entirety. Further, in some implementations in the case of an electronic cigarette, the cartridge may comprise a single-use cartridge, as disclosed in U.S. Pat. No. 8,910,639 to Chang et al., which is incorporated herein by reference.

One or more connections may be employed to connect the power source to a recharging technology, and some may involve a charging case, cradle, dock, sleeve or the like. More specifically, for example, the control body may be configured to engage a cradle that includes a USB connector to connect to a power supply. Or in another example, the control body may be configured to fit within and engage a sleeve that includes a USB connector to connect to a power supply. In these and similar examples, the USB connector may connect directly to the power source, or the USB connector may connect to the power source via a suitable power adapter.

Examples of power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference. With respect to the flow sensor, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. No. 8,881,737 to Collet et al., U.S. Pat. No. 9,423,152 to Ampolini et al., U.S. Pat. No. 9,439,454 to Fernando et al., and U.S. Pat. App. Pub. No. 2015/0257445 to Henry et al., all of which are incorporated herein by reference.

An input element may be included with the aerosol delivery device (and may replace or supplement a flow sensor). The input may be included to allow a user to control functions of the device and/or for output of information to a user. Any component or combination of components may be utilized as an input for controlling the function of the device. For example, one or more pushbuttons may be used as described in U.S. Pub. No. 2015/0245658 to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. Pub. 2016/0158782 to Henry et al., which is incorporated herein by reference. As still a further example, a capacitive sensor may be implemented on the aerosol delivery device to enable a user to provide input, such as by touching a surface of the device on which the capacitive sensor is implemented. In another example, a sensor capable of detecting a motion associated with the device (e.g., accelerometer, gyroscope, photoelectric proximity sensor, etc.) may be implemented on the aerosol delivery device to enable a user to provide input. Examples of suitable sensors are described in U.S. Pat. App. Pub. No. 2018/0132528 to Sur et al., and U.S. Pat. App. Pub. No. 2016/0158782 to Henry et al., which are incorporated herein by reference.

As indicated above, the aerosol delivery device may include various electronics such as at least one control component. A suitable control component may include a number of electronic components, and in some examples may be formed of a circuit board such as a printed circuit board (PCB). In some examples, the electronic components include processing circuitry configured to perform data processing, application execution, or other processing, control or management services according to one or more example implementations. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like.

In some examples, the control component may include one or more input/output peripherals, which may be coupled to or integrated with the processing circuitry. More particularly, the control component may include a communication interface to enable wireless communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

Still further components can be utilized in the aerosol delivery device of the present disclosure. One example of a suitable component is an indicator such as light-emitting diodes (LEDs), quantum dot-based LEDs, organic LEDs or the like, which may be illuminated with use of the aerosol delivery device. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. No. 9,451,791 to Sears et al., all of which are incorporated herein by reference.

Other indices of operation are also encompassed by the present disclosure. For example, visual indicators of operation also include changes in light color or intensity to show progression of the smoking experience. Tactile (haptic) indicators of operation and sound (audio) indicators of operation similarly are encompassed by the disclosure. Moreover, combinations of such indicators of operation also are suitable to be used in a single smoking article. According to another aspect, the aerosol delivery device may include one or more indicators or indicia, such as, for example, a display configured to provide information corresponding to the operation of the smoking article such as, for example, the amount of power remaining in the power source, progression of the smoking experience, indication corresponding to activating a heat source, and/or the like.

Yet other components are also contemplated. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference.

Further examples of components related to electronic aerosol delivery articles and disclosing materials or components that may be used in the present article include U.S. Pat. No. 4,735,217 to Gerth et al., U.S. Pat. No. 5,249,586 to Morgan et al., U.S. Pat. No. 5,666,977 to Higgins et al., U.S. Pat. No. 6,053,176 to Adams et al., U.S. Pat. No. 6,164,287 to White, U.S. Pat. No. 6,196,218 to Voges, U.S. Pat. No. 6,810,883 to Felter et al., U.S. Pat. No. 6,854,461 to Nichols, U.S. Pat. No. 7,832,410 to Hon, U.S. Pat. No. 7,513,253 to Kobayashi, U.S. Pat. No. 7,896,006 to Hamano, U.S. Pat. No. 6,772,756 to Shayan, U.S. Pat. No. 8,156,944 and 8,375,957 to Hon, U.S. Pat. No. 8,794,231 to Thorens et al., U.S. Pat. No. 8,851,083 to Oglesby et al., U.S. Pat. No. 8,915,254 and 8,925,555 to Monsees et al., U.S. Pat. No. 9,220,302 to DePiano et al., U.S. Pat. App. Pub. Nos. 2006/0196518 and 2009/0188490 to Hon, U.S. Pat. App. Pub. No. 2010/0024834 to Oglesby et al., U.S. Pat. App. Pub. No. 2010/0307518 to Wang, PCT Pat. App. Pub. No. WO 2010/091593 to Hon, and PCT Pat. App. Pub. No. WO 2013/089551 to Foo, each of which is incorporated herein by reference. Further, U.S. Pat. App. Pub. No. 2017/0099877 to Worm et al., discloses capsules that may be included in aerosol delivery devices and fob-shape configurations for aerosol delivery devices, and is incorporated herein by reference. A variety of the materials disclosed by the foregoing documents may be incorporated into the present devices in various implementations, and all of the foregoing disclosures are incorporated herein by reference.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. No. 8,689,804 to Fernando et al., U.S. Pat. App. Pub. No. 2013/0192623 to Tucker et al., U.S. Pat. No. 9,427,022 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. No. 9,220,302 to DePiano et al., all of which are incorporated herein by reference.

Figure 1:
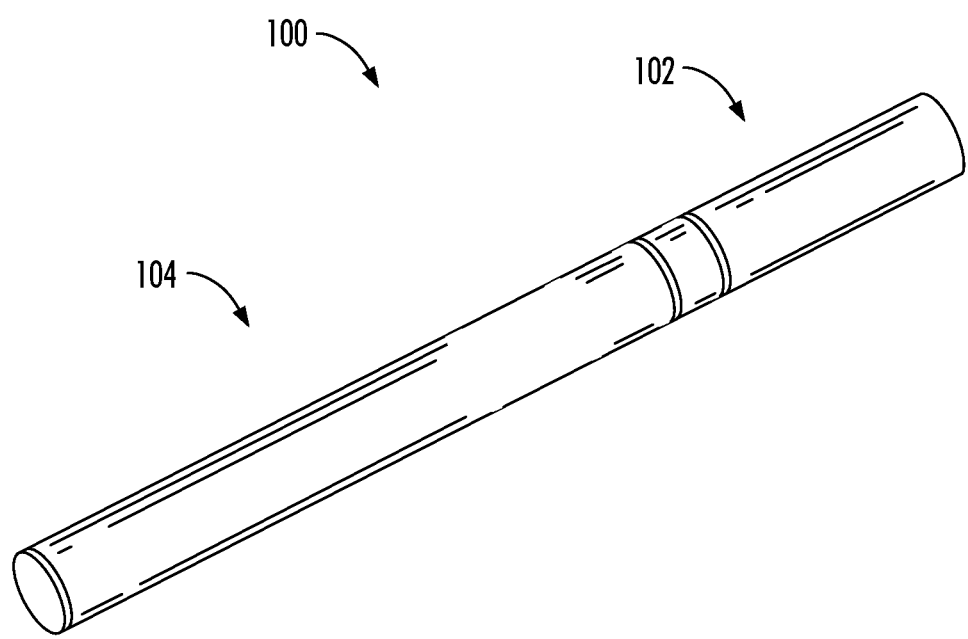
FIG. 1 illustrates a perspective view of an aerosol delivery device including a cartridge and a control body that are coupled to one another, according to an example implementation of the present disclosure.
Figure 2:
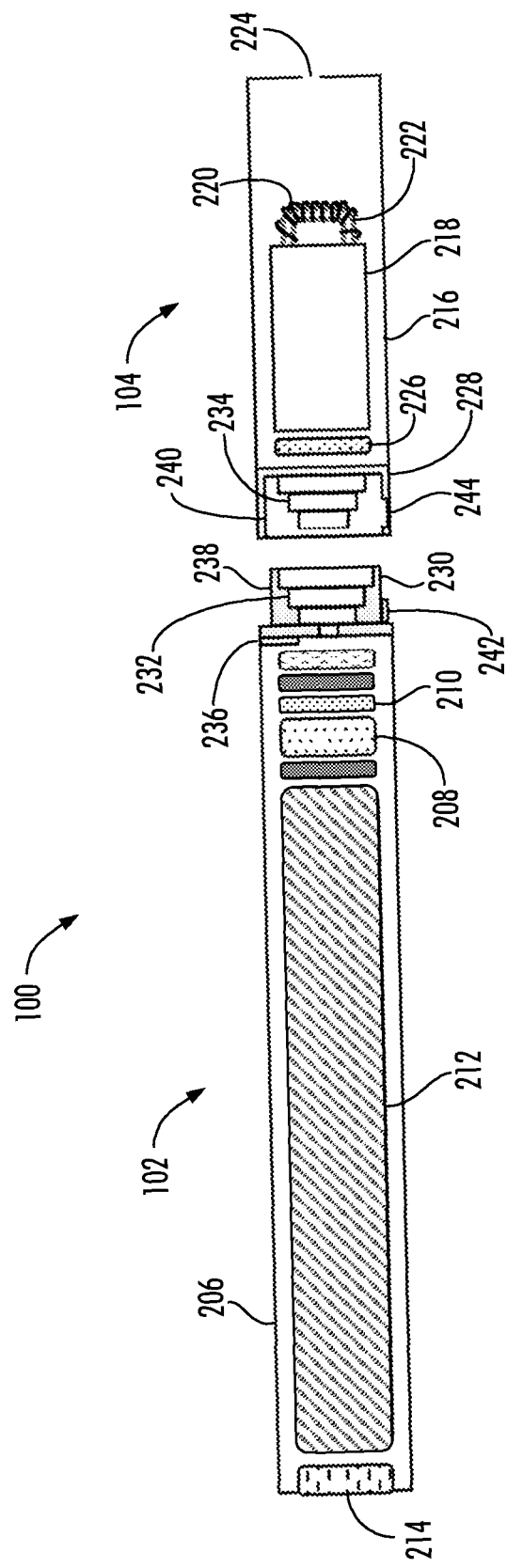
FIG. 2 is a partially cut-away view of the aerosol delivery device of FIG. 1 in which the cartridge and control body are decoupled from one another, according to an example implementation.

FIGS. 1 and 2 illustrate implementations of an aerosol delivery device including a control body and a cartridge in the case of an electronic cigarette. More specifically, FIGS. 1 and 2 illustrate an aerosol delivery device 100 according to an example implementation of the present disclosure. As indicated, the aerosol delivery device may include a control body 102 and a cartridge 104. The control body and the cartridge can be permanently or detachably aligned in a functioning relationship. In this regard, FIG. 1 illustrates a perspective view of the aerosol delivery device in a coupled configuration, whereas FIG. 2 illustrates a partially cut-away side view of the aerosol delivery device in a decoupled configuration. The aerosol delivery device may, for example, be substantially rod-like or rod-shaped, substantially tubular shaped, or substantially cylindrically shaped in some implementations when the control body and the cartridge are in an assembled configuration.

The control body 102 and the cartridge 104 can be configured to engage one another by a variety of connections, such as a press fit (or interference fit) connection, a threaded connection, a magnetic connection, or the like. As such, the control body may include a first engaging element (e.g., a coupler) that is adapted to engage a second engaging element (e.g., a connector) on the cartridge. The first engaging element and the second engaging element may be reversible. As an example, either of the first engaging element or the second engaging element may be a male thread, and the other may be a female thread. As a further example, either the first engaging element or the second engaging element may be a magnet, and the other may be a metal or a matching magnet. In particular implementations, engaging elements may be defined directly by existing components of the control body and the cartridge. For example, the housing of the control body may define a cavity at an end thereof that is configured to receive at least a portion of the cartridge (e.g., a storage tank or other shell-forming element of the cartridge). In particular, a storage tank of the cartridge may be at least partially received within the cavity of the control body while a mouthpiece of the cartridge remains exposed outside of the cavity of the control body. The cartridge may be retained within the cavity formed by the control body housing, such as by an interference fit (e.g., through use of detents and/or other features creating an interference engagement between an outer surface of the cartridge and an interior surface of a wall forming the control body cavity), by a magnetic engagement (e.g., though use of magnets and/or magnetic metals positioned within the cavity of the control body and positioned on the cartridge), or by other suitable techniques.

As seen in the cut-away view illustrated in FIG. 2, the control body 102 and cartridge 104 each include a number of respective components. The components illustrated in FIG. 2 are representative of the components that may be present in a control body and cartridge and are not intended to limit the scope of components that are encompassed by the present disclosure. As shown, for example, the control body can be formed of a housing 206 (sometimes referred to as a control body shell) that can include a control component 208 (e.g., processing circuitry, etc.), a flow sensor 210, a power source 212 (e.g., battery, supercapacitor), and an indicator 214 (e.g., LED, quantum dot-based LED, organic LED), and such components can be variably aligned.

The cartridge 104 can be formed of a housing 216 (sometimes referred to as the cartridge shell) enclosing a reservoir 218 configured to retain the aerosol precursor composition, and including a heating element 220 (sometimes referred to as a heater). In various configurations, this structure may be referred to as a tank; and accordingly, the terms "cartridge," "tank" and the like may be used interchangeably to refer to a shell or other housing enclosing a reservoir for aerosol precursor composition, and including a heating element.

As shown, in some examples, the reservoir 218 may be in fluid communication with a liquid transport element 222 adapted to wick or otherwise transport an aerosol precursor composition stored in the reservoir housing to the heating element 220. Other arrangements of liquid transport elements are contemplated within the scope of the disclosure. For example, in some implementations, a liquid transport element may be positioned proximate a distal end of the reservoir and arranged transverse to a longitudinal axis of the reservoir. In some examples, a valve may be positioned between the reservoir and heating element, and configured to control an amount of aerosol precursor composition passed or delivered from the reservoir to the heating element.

Various examples of materials configured to produce heat when electrical current is applied therethrough may be employed to form the heating element 220. The heating element in these examples may be a resistive heating element such as a wire coil, flat plate, micro heater or the like. Example materials from which the heating element may be formed include Kanthal (FeCrAl), nichrome, nickel, stainless steel, indium tin oxide, tungsten, molybdenum disilicide ($MoSi_2$), molybdenum silicide (MoSi), molybdenum disilicide doped with aluminum ($Mo(Si,Al)_2$), titanium, platinum, silver, palladium, alloys of silver and palladium, graphite and graphite-based materials (e.g., carbon-based foams and yarns), conductive inks, boron doped silica, and ceramics (e.g., positive or negative temperature coefficient ceramics).

The heating element may be resistive heating element or a heating element configured to generate heat through induction. The heating element may be coated by heat conductive ceramics such as aluminum nitride, silicon carbide, beryllium oxide, alumina, silicon nitride, or their composites. Example implementations of heating elements useful in aerosol delivery devices according to the present disclosure are further described below, and can be incorporated into devices such as those described herein.

An opening 224 may be present in the housing 216 (e.g., at the mouth end) to allow for egress of formed aerosol from the cartridge 104.

The cartridge 104 also may include one or more electronic components 226, which may include an integrated circuit, a memory component (e.g., EEPROM, flash memory), a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on a circuit board (e.g., PCB) that supports and electrically connects the electronic components. Further, the circuit board may be positioned horizontally relative the illustration of FIG. 1 in that the circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heating element 220 in the cartridge. Further, the housing 206 can include an air intake 236, which may be a notch in the housing where it connects to the coupler that allows for passage of ambient air around the coupler and into the housing where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the housing 216, in this example. An aerosol precursor composition can be retained in the reservoir. Liquid components, for example, can be sorptively retained by the reservoir. The reservoir can be in fluid connection with the liquid transport element 222. The liquid transport element can transport the aerosol precursor composition stored in the reservoir via capillary action—or via a micro pump—to the heating element 220 that is in the form of a metal wire coil in this example. As such, the heating element is in a heating arrangement with the liquid transport element.

In some examples, a microfluidic chip may be embedded in the reservoir 218, and the amount and/or mass of aerosol precursor composition delivered from the reservoir may be controlled by a micro pump, such as one based on microelectromechanical systems (MEMS) technology. Other example implementations of reservoirs and transport elements useful in aerosol delivery devices according to the present disclosure are further described herein, and such reservoirs and/or transport elements can be incorporated into devices such as those described herein. In particular, specific combinations of heating members and transport elements as further described herein may be incorporated into devices such as those described herein.

In use, when a user draws on the aerosol delivery device 100, airflow is detected by the flow sensor 210, and the heating element 220 is activated to vaporize components of the aerosol precursor composition. Drawing upon the mouth end of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heating element and out the opening 224 in the mouth end of the aerosol delivery device.

For further detail regarding implementations of an aerosol delivery device including a control body and a cartridge in the case of an electronic cigarette, see the above-cited U.S. patent application Ser. No. 15/836,086 to Sur, and U.S. patent application Ser. No. 15/916,834 to Sur et al., as well as U.S. patent application Ser. No. 15/916,696 to Sur, filed Mar. 9, 2018, which is also incorporated herein by reference.

Figure 3:
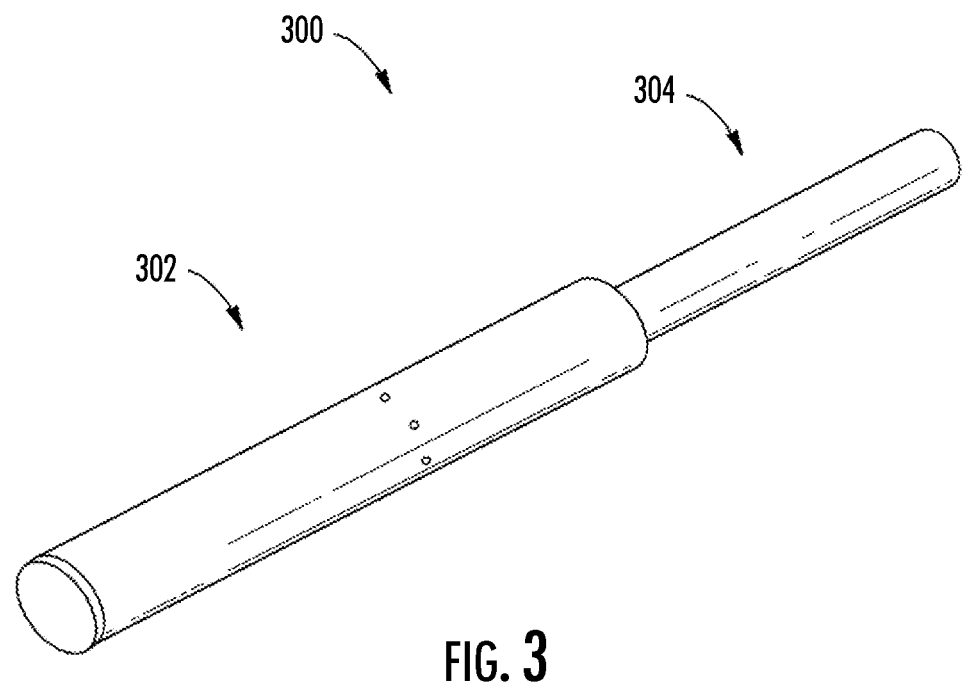
FIGS. 3 and 4 illustrate a perspective view of an aerosol delivery device comprising a control body and an aerosol source member that are respectively coupled to one another and decoupled from one another, according to another example implementation of the present disclosure.
Figure 4:
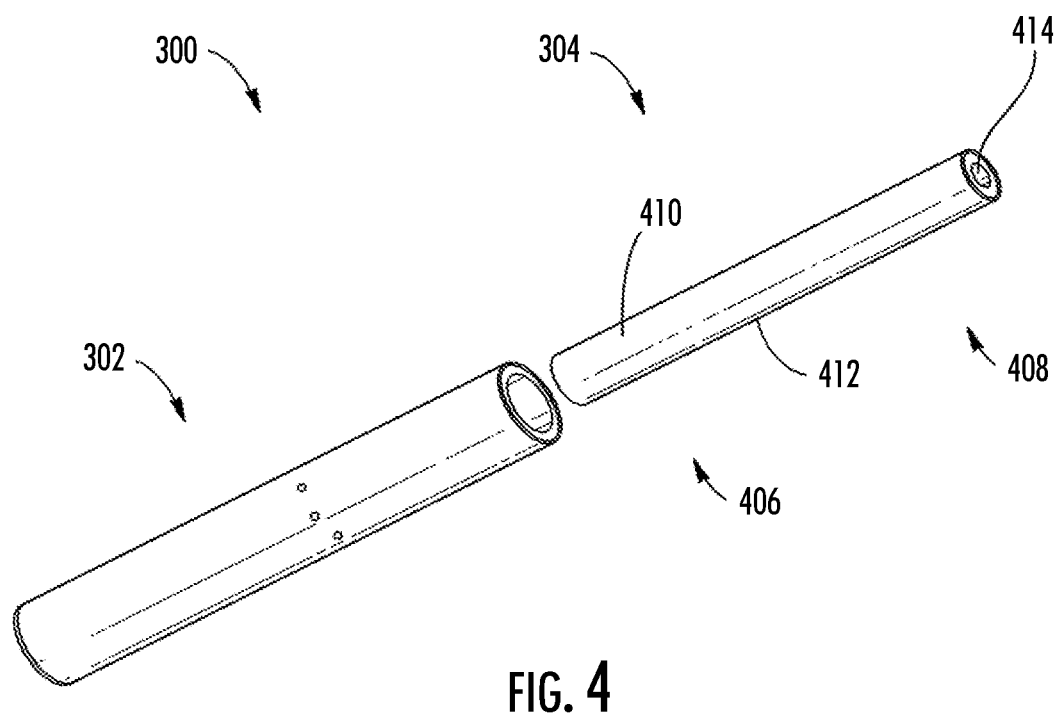

FIGS. 3-6 illustrate implementations of an aerosol delivery device including a control body and an aerosol source member in the case of a heat-not-burn device. More specifically, FIG. 3 illustrates an aerosol delivery device 300 according to an example implementation of the present disclosure. The aerosol delivery device may include a control body 302 and an aerosol source member 304. In various implementations, the aerosol source member and the control body can be permanently or detachably aligned in a functioning relationship. In this regard, FIG. 3 illustrates the aerosol delivery device in a coupled configuration, whereas FIG. 4 illustrates the aerosol delivery device in a decoupled configuration. Various mechanisms may connect the aerosol source member to the control body to result in a threaded engagement, a press-fit engagement, an interference fit, a sliding fit, a magnetic engagement, or the like.

As shown in FIG. 4, in various implementations of the present disclosure, the aerosol source member 304 may comprise a heated end 406, which is configured to be inserted into the control body 302, and a mouth end 408, upon which a user draws to create the aerosol. In various implementations, at least a portion of the heated end may include an aerosol precursor composition 410.

In various implementations, the aerosol source member 304, or a portion thereof, may be wrapped in an exterior overwrap material 412, which may be formed of any material useful for providing additional structure and/or support for the aerosol source member. In various implementations, the exterior overwrap material may comprise a material that resists transfer of heat, which may include a paper or other fibrous material, such as a cellulose material. The exterior overwrap material may also include at least one filler material imbedded or dispersed within the fibrous material. In various implementations, the filler material may have the form of water insoluble particles. Additionally, the filler material may incorporate inorganic components. In various implementations, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the overwrap at the mouth end 408 of the aerosol source member may function to simply separate the aerosol precursor composition 410 from the mouth of a consumer or to provide space for positioning of a filter material, as described below, or to affect draw on the article or to affect flow characteristics of the vapor or aerosol leaving the device during draw. Further discussion relating to the configurations for overwrap materials that may be used with the present disclosure may be found in the above-cited U.S. Pat. No. 9,078,473 to Worm et al.

In various implementations other components may exist between the aerosol precursor composition 410 and the mouth end 408 of the aerosol source member 304, wherein the mouth end may include a filter 414, which may, for example, be made of a cellulose acetate or polypropylene material. The filter may additionally or alternatively, contain strands of tobacco containing material, such as described in U.S. Pat. No. 5,025,814 to Raker et al., which is incorporated herein by reference in its entirety. In various implementations, the filter may increase the structural integrity of the mouth end of the aerosol source member, and/or provide filtering capacity, if desired, and/or provide resistance to draw. In some implementations one or any combination of the following may be positioned between the aerosol precursor composition and the mouth end: an air gap; phase change materials for cooling air; flavor releasing media; ion exchange fibers capable of selective chemical adsorption; aerogel particles as filter medium; and other suitable materials.

Various implementations of the present disclosure employ one or more conductive heating elements to heat the aerosol precursor composition 410 of the aerosol source member 304. In various implementations, the heating element may be provided in a variety forms, such as in the form of a foil, a foam, a mesh, a hollow ball, a half ball, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in direct contact with, or in proximity to, the aerosol source member and particularly, the aerosol precursor composition of the aerosol source member 304. The heating element may be located in the control body and/or the aerosol source member. In various implementations, the aerosol precursor composition may include components (i.e., heat conducting constituents) that are imbedded in, or otherwise part of, the substrate portion that may serve as, or facilitate the function of, the heating assembly. Some examples of various heating members and elements are described in U.S. Pat. No. 9,078,473 to Worm et al.

Some non-limiting examples of various heating element configurations include configurations in which a heating element is placed in proximity with the aerosol source member 304. For instance, in some examples, at least a portion of a heating element may surround at least a portion of an aerosol source member. In other examples, one or more heating elements may be positioned adjacent an exterior of an aerosol source member when inserted in the control body 302. In other examples, at least a portion of a heating element may penetrate at least a portion of an aerosol source member (such as, for example, one or more prongs and/or spikes that penetrate an aerosol source member), when the aerosol source member is inserted into the control body. In some instances, the aerosol precursor composition may include a structure in contact with, or a plurality of beads or particles imbedded in, or otherwise part of, the aerosol precursor composition that may serve as, or facilitate the function of the heating element.

Figure 5:
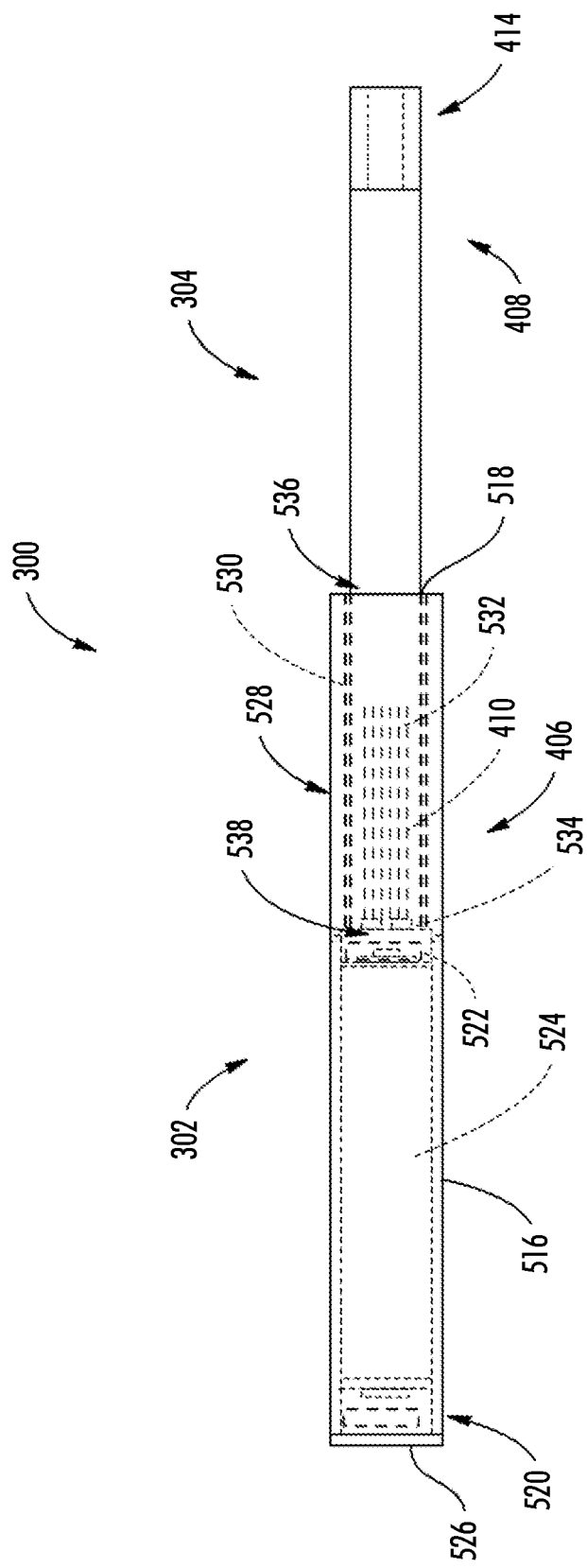
FIGS. 5 and 6 illustrate respectively a front view of and a sectional view through the aerosol delivery device of FIGS. 3 and 4, according to an example implementation.
Figure 6:
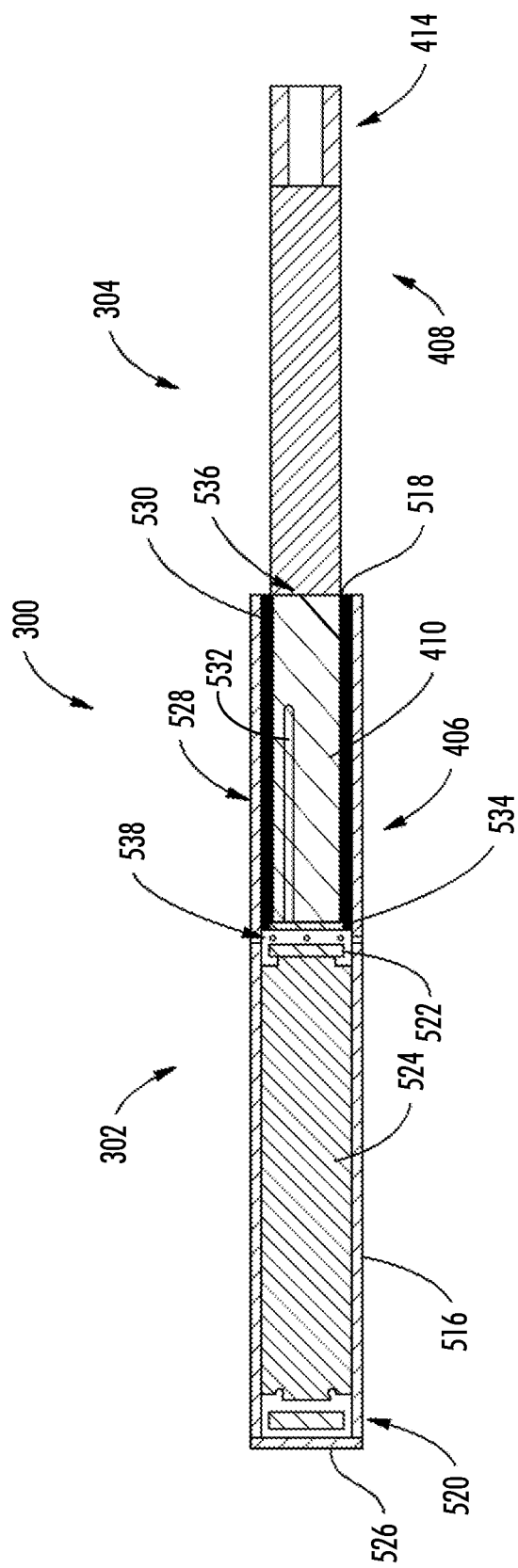
Figure 7:
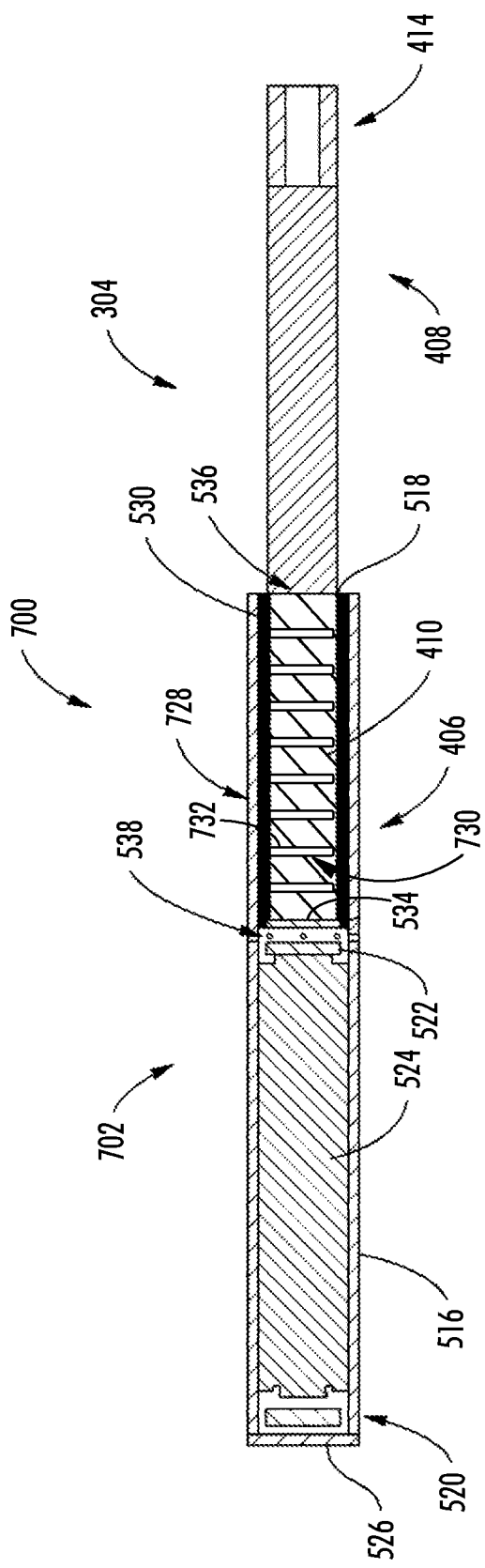
FIG. 7 illustrates a sectional view of an aerosol delivery device according to another example implementation.
Figure 8:
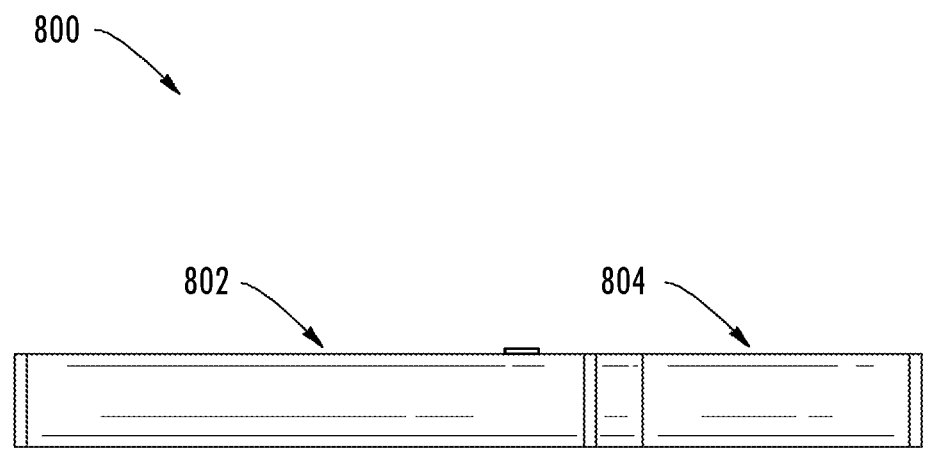
FIGS. 8 and 9 illustrate respectively a side view and a partially cut-away view of an aerosol delivery device including a cartridge coupled to a control body, according to example implementations.

FIG. 5 illustrates a front view of an aerosol delivery device 300 according to an example implementation of the present disclosure, and FIG. 6 illustrates a sectional view through the aerosol delivery device of FIG. 5. In particular, the control body 302 of the depicted implementation may comprise a housing 516 that includes an opening 518 defined in an engaging end thereof, a flow sensor 520 (e.g., a puff sensor or pressure switch), a control component 522 (e.g., processing circuitry, etc.), a power source 524 (e.g., battery, supercapacitor), and an end cap that includes an indicator 526.

In one implementation, the indicator 526 may comprise one or more LEDs, quantum dot-based LEDs, organic LEDs or the like. The indicator can be in communication with the control component 522 and be illuminated, for example, when a user draws on the aerosol source member 304, when coupled to the control body 302, as detected by the flow sensor 520.

The control body 302 of the depicted implementation includes one or more heating assemblies 528 (individually or collectively referred to a heating assembly) configured to heat the aerosol precursor composition 410 of the aerosol source member 304. Although the heating assembly of various implementations of the present disclosure may take a variety of forms, in the particular implementation depicted in FIGS. 5 and 6, the heating assembly comprises an outer cylinder 530 and a heating element 532, which in this implementation comprises a plurality of heater prongs that extend from a receiving base 534 (in various configurations, the heating assembly or more specifically the heater prongs may be referred to as a heater). In the depicted implementation, the outer cylinder comprises a double-walled vacuum tube constructed of stainless steel so as to maintain heat generated by the heater prongs within the outer cylinder, and more particularly, maintain heat generated by heater prongs within the aerosol precursor composition. In various implementations, the heater prongs may be constructed of one or more conductive materials, including, but not limited to, copper, aluminum, platinum, gold, silver, iron, steel, brass, bronze, graphite, or any combination thereof.

As illustrated, the heating assembly 528 may extend proximate an engagement end of the housing 516, and may be configured to substantially surround a portion of the heated end 406 of the aerosol source member 304 that includes the aerosol precursor composition 410, In such a manner, the heating assembly may define a generally tubular configuration. As illustrated in FIGS. 5 and 6, the heating element 532 (e.g., plurality of heater prongs) is surrounded by the outer cylinder 530 to create a receiving chamber 536. In such a manner, in various implementations the outer cylinder may comprise a nonconductive insulating material and/or construction including, but not limited to, an insulating polymer (e.g., plastic or cellulose), glass, rubber, ceramic, porcelain, a double-walled vacuum structure, or any combinations thereof.

In some implementations, one or more portions or components of the heating assembly 528 may be combined with, packaged with, and/or integral with (e.g., embedded within) the aerosol precursor composition 410. For example, in some implementations the aerosol precursor composition may be formed of a material as described above and may include one or more conductive materials mixed therein. In some of these implementations, contacts may be connected directly to the aerosol precursor composition such that, when the aerosol source member is inserted into the receiving chamber of the control body, the contacts make electrical connection with the electrical energy source. Alternatively, the contacts may be integral with the electrical energy source and may extend into the receiving chamber such that, when the aerosol source member is inserted into the receiving chamber of the control body, the contacts make electrical connection with the aerosol precursor composition. Because of the presence of the conductive material in the aerosol precursor composition, the application of power from the electrical energy source to the aerosol precursor composition allows electrical current to flow and thus produce heat from the conductive material. Thus, in some implementations the heating element may be described as being integral with the aerosol precursor composition. As a non-limiting example, graphite or other suitable, conductive material may be mixed with, embedded in, or otherwise present directly on or within the material forming the aerosol precursor composition to make the heating element integral with the medium.

As noted above, in the illustrated implementation, the outer cylinder 530 may also serve to facilitate proper positioning of the aerosol source member 304 when the aerosol source member is inserted into the housing 516. In various implementations, the outer cylinder of the heating assembly 528 may engage an internal surface of the housing to provide for alignment of the heating assembly with respect to the housing. Thereby, as a result of the fixed coupling between the heating assembly, a longitudinal axis of the heating assembly may extend substantially parallel to a longitudinal axis of the housing. In particular, the support cylinder may extend from the opening 518 of the housing to the receiving base 534 to create the receiving chamber 536.

The heated end 406 of the aerosol source member 304 is sized and shaped for insertion into the control body 302. In various implementations, the receiving chamber 536 of the control body may be characterized as being defined by a wall with an inner surface and an outer surface, the inner surface defining the interior volume of the receiving chamber. For example, in the depicted implementations, the outer cylinder 530 defines an inner surface defining the interior volume of the receiving chamber. In the illustrated implementation, an inner diameter of the outer cylinder may be slightly larger than or approximately equal to an outer diameter of a corresponding aerosol source member (e.g., to create a sliding fit) such that the outer cylinder is configured to guide the aerosol source member into the proper position (e.g., lateral position) with respect to the control body. Thus, the largest outer diameter (or other dimension depending upon the specific cross-sectional shape of the implementations) of the aerosol source member may be sized to be less than the inner diameter (or other dimension) at the inner surface of the wall of the open end of the receiving chamber in the control body. In some implementations, the difference in the respective diameters may be sufficiently small so that the aerosol source member fits snugly into the receiving chamber, and frictional forces prevent the aerosol source member from being moved without an applied force. On the other hand, the difference may be sufficient to allow the aerosol source member to slide into or out of the receiving chamber without requiring undue force.

In the illustrated implementation, the control body 302 is configured such that when the aerosol source member 304 is inserted into the control body, the heating element 532 (e.g., heater prongs) is located in the approximate radial center of at least a portion of the aerosol precursor composition 410 of the heated end 406 of the aerosol source member. In such a manner, when used in conjunction with a solid or semi-solid aerosol precursor composition, the heater prongs may be in direct contact with the aerosol precursor composition. In other implementations, such as when used in conjunction with an extruded aerosol precursor composition that defines a tube structure, the heater prongs may be located inside of a cavity defined by an inner surface of the extruded tube structure, and would not contact the inner surface of the extruded tube structure.

During use, the consumer initiates heating of the heating assembly 528, and in particular, the heating element 532 that is adjacent the aerosol precursor composition 410 (or a specific layer thereof). Heating of the aerosol precursor composition releases the inhalable substance within the aerosol source member 304 so as to yield the inhalable substance. When the consumer inhales on the mouth end 408 of the aerosol source member, air is drawn into the aerosol source member through an air intake 538 such as openings or apertures in the control body 302. The combination of the drawn air and the released inhalable substance is inhaled by the consumer as the drawn materials exit the mouth end of the aerosol source member. In some implementations, to initiate heating, the consumer may manually actuate a push-button or similar component that causes the heating element of the heating assembly to receive electrical energy from the battery or other energy source. The electrical energy may be supplied for a pre-determined length of time or may be manually controlled.

In some implementations, flow of electrical energy does not substantially proceed in between puffs on the device 300 (although energy flow may proceed to maintain a baseline temperature greater than ambient temperature—e.g., a temperature that facilitates rapid heating to the active heating temperature). In the depicted implementation, however, heating is initiated by the puffing action of the consumer through use of one or more sensors, such as flow sensor 520. Once the puff is discontinued, heating will stop or be reduced. When the consumer has taken a sufficient number of puffs so as to have released a sufficient amount of the inhalable substance (e.g., an amount sufficient to equate to a typical smoking experience), the aerosol source member 304 may be removed from the control body 302 and discarded. In some implementations, further sensing elements, such as capacitive sensing elements and other sensors, may be used as discussed in U.S. patent application Ser. No. 15/707,461 to Phillips et al., which is incorporated herein by reference.

In various implementations, the aerosol source member 304 may be formed of any material suitable for forming and maintaining an appropriate conformation, such as a tubular shape, and for retaining therein the aerosol precursor composition 410. In some implementations, the aerosol source member may be formed of a single wall or, in other implementations, multiple walls, and may be formed of a material (natural or synthetic) that is heat resistant so as to retain its structural integrity—e.g., does not degrade—at least at a temperature that is the heating temperature provided by the electrical heating element, as further discussed herein. While in some implementations, a heat resistant polymer may be used, in other implementations, the aerosol source member may be formed from paper, such as a paper that is substantially straw-shaped. As further discussed herein, the aerosol source member may have one or more layers associated therewith that function to substantially prevent movement of vapor therethrough. In one example implementation, an aluminum foil layer may be laminated to one surface of the aerosol source member. Ceramic materials also may be used. In further implementations, an insulating material may be used so as not to unnecessarily move heat away from the aerosol precursor composition. Further example types of components and materials that may be used to provide the functions described above or be used as alternatives to the materials and components noted above can be those of the types set forth in U.S. Pat. App. Pub. Nos. 2010/00186757 to Crooks et al., 2010/00186757 to Crooks et al., and 2011/0041861 to Sebastian et al., all of which are incorporated herein by reference.

In the depicted implementation, the control body 302 includes a control component 522 that controls the various functions of the aerosol delivery device 300, including providing power to the electrical heating element 532. For example, the control component may include processing circuitry (which may be connected to further components, as further described herein) that is connected by electrically conductive wires (not shown) to the power source 524. In various implementations, the processing circuitry may control when and how the heating assembly 528, and particularly the heater prongs, receives electrical energy to heat the aerosol precursor composition 410 for release of the inhalable substance for inhalation by a consumer. In some implementations, such control may be activated by a flow sensor 520 as described in greater detail above.

As seen in FIGS. 5 and 6, the heating assembly 528 of the depicted implementation comprises an outer cylinder 530 and a heating element 532 (e.g., plurality of heater prongs) that extend from a receiving base 534. In some implementations, such as those wherein the aerosol precursor composition 410 comprises a tube structure, the heater prongs may be configured to extend into a cavity defined by the inner surface of the aerosol precursor composition. In other implementations, such as the depicted implementation wherein the aerosol precursor composition comprises a solid or semi-solid, the plurality of heater prongs is configured to penetrate into the aerosol precursor composition contained in the heated end 406 of the aerosol source member 304 when the aerosol source member is inserted into the control body 302. In such implementations, one or more of the components of the heating assembly, including the heater prongs and/or the receiving base, may be constructed of a non-stick or stick-resistant material, for example, certain aluminum, copper, stainless steel, carbon steel, and ceramic materials. In other implementations, one or more of the components of the heating assembly, including the heater prongs and/or the receiving base, may include a non-stick coating, including, for example, a polytetrafluoroethylene (PTFE) coating, such as Teflon®, or other coatings, such as a stick-resistant enamel coating, or a ceramic coating, such as Greblon®, or Thermolon™, or a ceramic coating, such as Greblon®, or Thermolon™.

In addition, although in the depicted implementation there are multiple heater prongs 532 that are substantially equally distributed about the receiving base 534, it should be noted that in other implementations, any number of heater prongs may be used, including as few as one, with any other suitable spatial configuration. Furthermore, in various implementations the length of the heater prongs may vary. For example, in some implementations the heater prongs may comprise small projections, while in other implementations the heater prongs may extend any portion of the length of the receiving chamber 536, including up to about 25%, up to about 50%, up to about 75%, and up to about the full length of the receiving chamber. In still other implementations, the heating assembly 528 may take on other configurations. Examples of other heater configurations that may be adapted for use in the present invention per the discussion provided above can be found in U.S. Pat. No. 5,060,671 to Counts et al., U.S. Pat. No. 5,093,894 to Deevi et al., U.S. Pat. No. 5,224,498 to Deevi et al., U.S. Pat. No. 5,228,460 to Sprinkel Jr., et al., U.S. Pat. No. 5,322,075 to Deevi et al., U.S. Pat. No. 5,353,813 to Deevi et al., U.S. Pat. No. 5,468,936 to Deevi et al., U.S. Pat. No. 5,498,850 to Das, U.S. Pat. No. 5,659,656 to Das, U.S. Pat. No. 5,498,855 to Deevi et al., U.S. Pat. No. 5,530,225 to Hajaligol, U.S. Pat. No. 5,665,262. to Hajaligol, U.S. Pat. No. 5,573,692 to Das et al.; and U.S. Pat. No. 5,591,368 to Fleischhauer et al., which are incorporated herein by reference.

In various implementations, the control body 302 may include an air intake 538 (e.g., one or more openings or apertures) therein for allowing entrance of ambient air into the interior of the receiving chamber 536. In such a manner, in some implementations the receiving base 534 may also include an air intake. Thus, in some implementations when a consumer draws on the mouth end of the aerosol source member 304, air can be drawn through the air intake of the control body and the receiving base into the receiving chamber, pass into the aerosol source member, and be drawn through the aerosol precursor composition 410 of the aerosol source member for inhalation by the consumer. In some implementations, the drawn air carries the inhalable substance through the optional filter 414 and out of an opening at the mouth end 408 of the aerosol source member, With the heating element 532 positioned inside the aerosol precursor composition, the heater prongs may be activated to heat the aerosol precursor composition and cause release of the inhalable substance through the aerosol source member.

As described above with reference to FIGS. 5 and 6 in particular, various implementations of the present disclosure employ a conductive heater to heat the aerosol precursor composition 410. As also indicated above, various other implementations employ an induction heater to heat the aerosol precursor composition. In some of these implementations, the heating assembly 528 may be configured as an induction heater that comprises a transformer with an induction transmitter and an induction receiver. In implementations in which the heating assembly is configured as the induction heater, the outer cylinder 530 may be configured as the induction transmitter, and the heating element 532 (e.g., plurality of heater prongs) that extend from the receiving base 534 may be configured as the induction receiver. In various implementations, one or both of the induction transmitter and induction receiver may be located in the control body 302 and/or the aerosol source member 304.

In various implementations, the outer cylinder 530 and heating element 532 as the induction transmitter and induction receiver may be constructed of one or more conductive materials, and in further implementations the induction receiver may be constructed of a ferromagnetic material including, but not limited to, cobalt, iron, nickel, and combinations thereof. In one example implementation, the foil material is constructed of a conductive material and the heater prongs are constructed of a ferromagnetic material. In various implementations, the receiving base may be constructed of a non-conductive and/or insulating material.

The outer cylinder 530 as the induction transmitter may include a laminate with a foil material that surrounds a support cylinder. In some implementations, the foil material may include an electrical trace printed thereon, such as, for example, one or more electrical traces that may, in some implementations, form a helical coil pattern when the foil material is positioned around the heating element 532 as the induction receiver. The foil material and support cylinder may each define a tubular configuration. The support cylinder may be configured to support the foil material such that the foil material does not move into contact with, and thereby short-circuit with, the heater prongs. In such a manner, the support cylinder may comprise a nonconductive material, which may be substantially transparent to an oscillating magnetic field produced by the foil material. In various implementations, the foil material may be imbedded in, or otherwise coupled to, the support cylinder. In the illustrated implementation, the foil material is engaged with an outer surface of the support cylinder; however, in other implementations, the foil material may be positioned at an inner surface of the support cylinder or be fully imbedded in the support cylinder.

The foil material of the outer cylinder 530 may be configured to create an oscillating magnetic field (e.g., a magnetic field that varies periodically with time) when alternating current is directed through it. The heater prongs of the heating element 532 may be at least partially located or received within the outer cylinder and include a conductive material. By directing alternating current through the foil material, eddy currents may be generated in the heater prongs via induction. The eddy currents flowing through the resistance of the material defining the heater prongs may heat it by Joule heating (i.e., through the Joule effect). The heater prongs may be wirelessly heated to form an aerosol from the aerosol precursor composition 410 positioned in proximity to the heater prongs.

FIG. 7 illustrates a sectional view of an aerosol delivery device 700 according to another example implementation. The aerosol delivery device 700 of FIG. 7 is similar to the aerosol delivery device 300 of FIGS. 3-6, and is particularly suited for segmented heating of the aerosol precursor composition 410. The aerosol delivery device 700 includes a control body 702 similar to control body 302 but including one or more heating assemblies 728 (individually or collectively referred to a heating assembly) configured to heat the aerosol precursor composition of the aerosol source member 304.

In the particular implementation depicted in FIG. 7, the heating assembly comprises an outer cylinder 530 and a segmented heater 730 including a plurality of heating elements 732 such as a plurality of electrically-conductive prongs (heater prongs) that are physically separate and spaced apart from one another. In some examples, each prong of the plurality of electrically-conductive prongs is a heating element of the plurality of heating elements of the segmented heater. In another example, the plurality of heating elements may be or include physically-isolated resistive heating elements that may be positioned adjacent respective exterior surface regions of the aerosol source member. In yet another example, the plurality of heating elements may be or include physically-isolated coils capable of producing localized/regionalized eddy currents in respective sections of the aerosol source member.

In examples in which the plurality of heating elements 732 are a plurality of heater prongs, these heater prongs may extend along and radially inward from an inner surface of the outer cylinder 330, and thereby lengthwise along the aerosol precursor composition 410. In the depicted implementation, the outer cylinder comprises a double-walled vacuum tube constructed of stainless steel so as to maintain heat generated by the heating elements (e.g., heater prongs) within the outer cylinder, and more particularly, maintain heat generated by heating elements within the aerosol precursor composition. Similar to above, in various implementations, the heating elements may be constructed of one or more conductive materials, including, but not limited to, copper, aluminum, platinum, gold, silver, iron, steel, brass, bronze, graphite, or any combination thereof In some examples the heating elements 732 of the segmented heater 730 may be powerable to heat a plurality of sections of the aerosol precursor composition 410. The heating elements may be concurrently powered to heat respective sections of the plurality of sections of the aerosol precursor composition, In some examples, heating elements of the plurality of heating elements may be separately powerable. In some of these examples, one or more of the heating elements may be separately powered to heat respective one or more sections of the plurality of sections of the aerosol precursor composition, and any other heating elements of the plurality of heating elements being simultaneously unpowered.

Other implementations of the aerosol delivery device, control body and aerosol source member are described in the above-cited U.S. patent application Ser. No. 15/916,834 to Sur et al., U.S. patent application Ser. No. 15/916,696 to Sur, U.S. patent application Ser. No. 15/836,086 to Sur, and U.S. patent application Ser. No. 15/976,526 to Sur, all of which are incorporated herein by reference.

FIGS. 8 and 9 illustrate implementations of an aerosol delivery device including a control body and a cartridge in the case of a no-heat-no-burn device. In this regard, FIG. 8 illustrates a side view of an aerosol delivery device 800 including a control body 802 and a cartridge 804, according to various example implementations of the present disclosure. In particular, FIG. 8 illustrates the control body and the cartridge coupled to one another. The control body and the cartridge may be detachably aligned in a functioning relationship.

FIG. 9 more particularly illustrates the aerosol delivery device 800, in accordance with some example implementations. As seen in the cut-away view illustrated therein, again, the aerosol delivery device can comprise a control body 802 and a cartridge 804 each of which include a number of respective components. The components illustrated in FIG.

9 are representative of the components that may be present in a control body and cartridge and are not intended to limit the scope of components that are encompassed by the present disclosure. As shown, for example, the control body can be formed of a control body housing or shell 906 that can include a control component 908 (e.g., processing circuitry, etc.), an input device 910, a power source 912 and an indicator 914 (e.g., LED, quantum dot-based LED, organic LED), and such components can be variably aligned. Here, a particular example of a suitable control component includes the PIC16(L)F1713/6 microcontrollers from Microchip Technology Inc., which is described in Microchip Technology, Inc., AN2265, *Vibrating Mesh Nebulizer Reference Design* (2016), which is incorporated by reference.

The cartridge 804 can be formed of a housing—referred to at times as a cartridge shell 916—enclosing a reservoir 918 configured to retain the aerosol precursor composition, and including a nozzle 920 having at least one piezoelectric/piezomagnetic mesh (aerosol production component). Similar to above, in various configurations, this structure may be referred to as a tank; and accordingly, the terms "cartridge," "tank" and the like may be used interchangeably to refer to a shell or other housing enclosing a reservoir for aerosol precursor composition, and including a nozzle.

Figure 9:
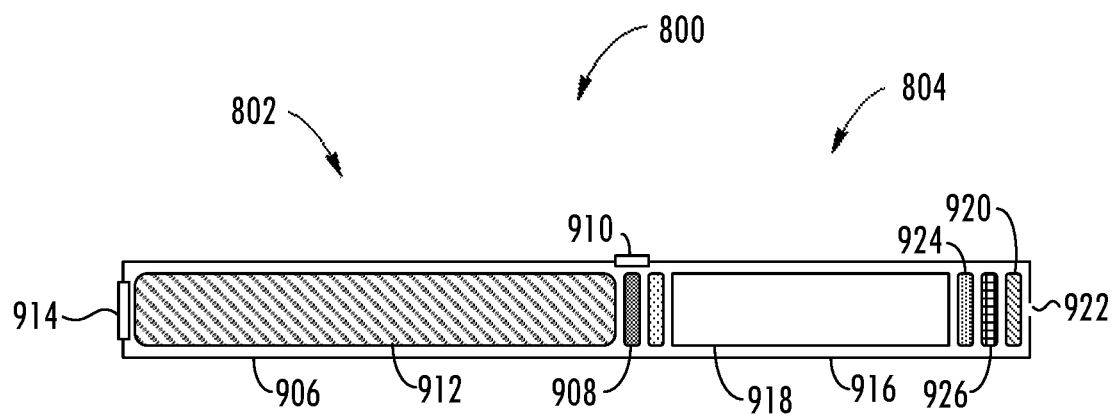

The reservoir 918 illustrated in FIG. 9 can be a container or can be a fibrous reservoir, as presently described. The reservoir may be in fluid communication with the nozzle 920 for transport of an aerosol precursor composition stored in the reservoir housing to the nozzle. An opening 922 may be present in the cartridge shell 916 (e.g., at the mouthend) to allow for egress of formed aerosol from the cartridge 804.

In some examples, a transport element may be positioned between the reservoir 918 and nozzle 920, and configured to control an amount of aerosol precursor composition passed or delivered from the reservoir to the nozzle. In some examples, a microfluidic chip may be embedded in the cartridge 804, and the amount and/or mass of aerosol precursor composition delivered from the reservoir may be controlled by one or more microfluidic components. One example of a microfluidic component is a micro pump 924, such as one based on microelectromechanical systems (MEMS) technology. Examples of suitable micro pumps include the model MDP2205 micro pump and others from thinXXS Microtechnology AG, the mp5 and mp6 model micro pumps and others from Bartels Mikrotechnik GmbH, and piezoelectric micro pumps from Takasago Fluidic Systems.

As also shown, in some examples, a micro filter 926 may be positioned between the micro pump 924 and nozzle 920 to filter aerosol precursor composition delivered to the nozzle. Like the micro pump, the micro filter is a microfluidic component. Examples of suitable micro filters include flow-through micro filters those manufactured using lab-on-a-chip (LOC) techniques.

In use, when the input device 910 detects user input to activate the aerosol delivery device, the piezoelectric/piezomagnetic mesh is activated to vibrate and thereby draw aerosol precursor composition through the mesh. This forms droplets of aerosol precursor composition that combine with air to form an aerosol. The aerosol is whisked, aspirated or otherwise drawn away from the mesh and out the opening 922 in the mouthend of the aerosol delivery device.

The aerosol delivery device 800 can incorporate the input device 910 such as a switch, sensor or detector for control of supply of electric power to the at least one piezoelectric/piezomagnetic mesh of the nozzle 920 when aerosol generation is desired (e.g., upon draw during use). As such, for example, there is provided a manner or method of turning off power to the mesh when the aerosol delivery device is not being drawn upon during use, and for turning on power to actuate or trigger the production and dispensing of aerosol from the nozzle during draw. Additional representative types of sensing or detection mechanisms, structure and configuration thereof, components thereof, and general methods of operation thereof, are described above and in U.S. Pat. No. 5,261,424 to Sprinkel, Jr., U.S. Pat. No. 5,372,148 to McCafferty et al., and PCT Pat. App. Pub. No. WO2010/003480 to Flick, all of which are incorporated herein by reference.

For more information regarding the above and other implementations of an aerosol delivery device in the case of a no-heat-no-burn device, see U.S. patent application Ser. No. 15/651,548 to Sur, filed Jul. 17, 2017, which is incorporated herein by reference.

Figure 10:
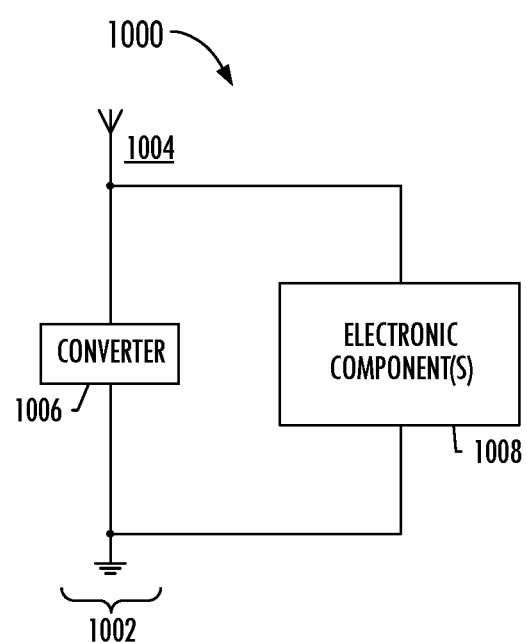

As described above, the aerosol delivery device of example implementations may include various electronic components in the context of an electronic cigarette, heat-not-burn device or no-heat-no-burn device, or even in the case of a device that includes the functionality of one or more of an electronic cigarette, heat-not-burn device or no-heat-no-burn device. FIG. 10 illustrates a circuit diagram of circuitry 1000 that may be implemented on and/or incorporate functionality of any one or more of aerosol delivery device 100, 300, 700, and 800 according to various example implementations of the present disclosure. In some more particular examples, the circuit diagram illustrates circuitry that may be implemented on and/or incorporate functionality of any one or more of control body 102, 302, 702 or 802. Additionally or alternatively, in some examples, the circuit diagram is of circuitry that may be implemented on a cartridge of an aerosol delivery device, such as cartridge 104, 804.

As shown in FIG. 10, in some examples, the circuitry 1000 includes power harvesting circuity 1002 for powering or charging at least one electronic component 1008 of an aerosol delivery device, such as one or more components of a control body, cartridge, or both a control body and cartridge. As described above, an aerosol delivery device may include various circuitry and electronic components such as a control component, sensor, power source, aerosol production component and the like. In some more particular examples, then, the at least one electronic component may include one or more of control component 208, 522, 908, flow sensor 210, 520, input device 910, power source 212, 524, 912, heating element(s) 220, 532, 732, or piezoelectric/piezomagnetic mesh of nozzle 920, Other examples of suitable electronic components include an accelerometer, gyroscope, proximity sensor, display (e.g., LED display), and the like.

The power harvesting circuitry 1002 may include an antenna 1004 configured to receive radio-frequency (RF) energy from an external RF transmitter, and a converter 1006 configured to harvest power from the RF energy. In some example implementations, the power harvesting circuitry may be configured to harvest power from the RF energy within a frequency range of 800 to 1000 megahertz (MHz).

Examples of suitable power harvesting circuitries are disclosed in U.S. Pat. No. 10,231,485 to Sur; U.S. Pat. No. 7,084,605 to Mickle et al.; and. U.S. Pat. App. Pub. No. 2011/0101789 to Salter, Jr. et al., each of which is incorporated herein by reference in its entirety. Further examples of suitable power harvesting circuitries are disclosed in Priya, Shashank, and Daniel J. Inman, eds., ENERGY HARVESTING TECHNOLOGIES, Vol. 21: 280-321, New York: Springer, 2009. Other power harvesting circuits that may he employed include the power harvesting circuits that have been incorporated in the Powerharvester™ receiver products by Powercast™.

Figure 11:
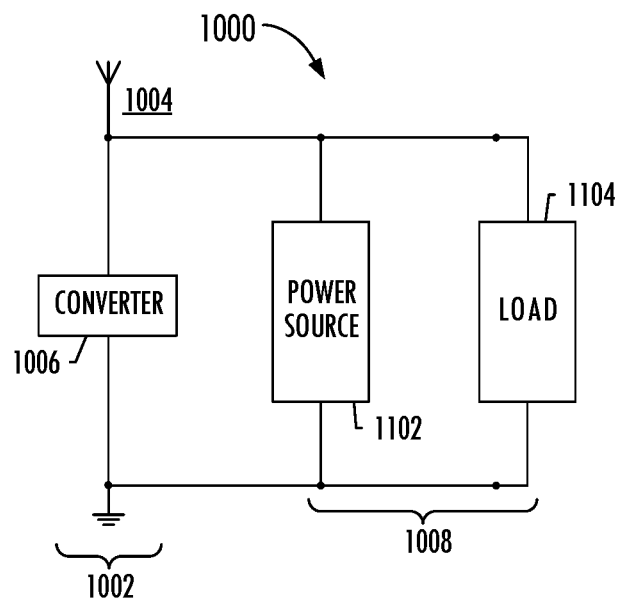
Figure 12:
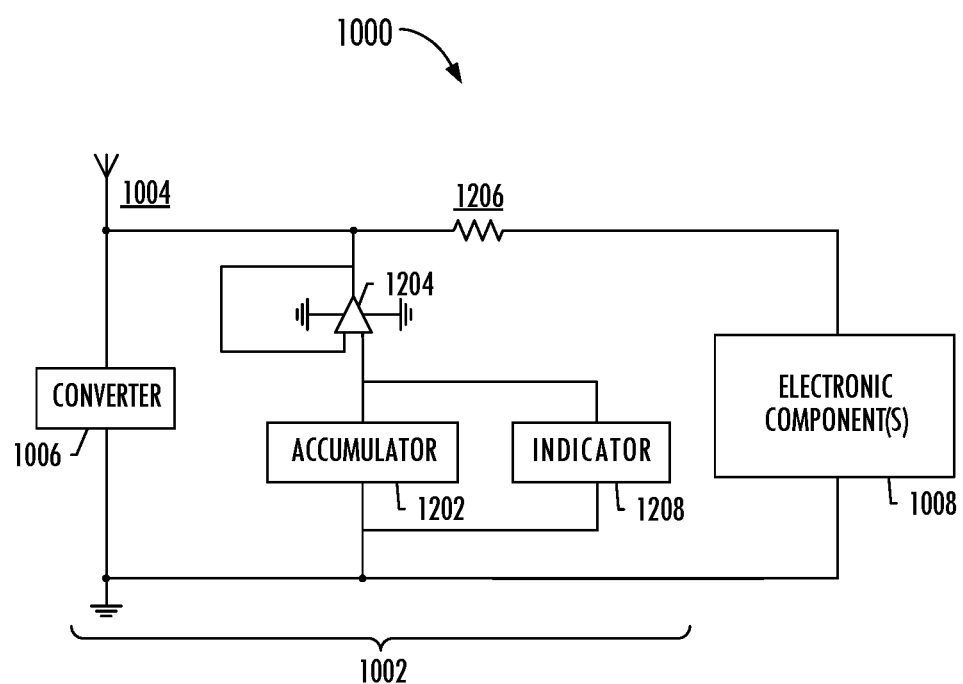
Figure 13:
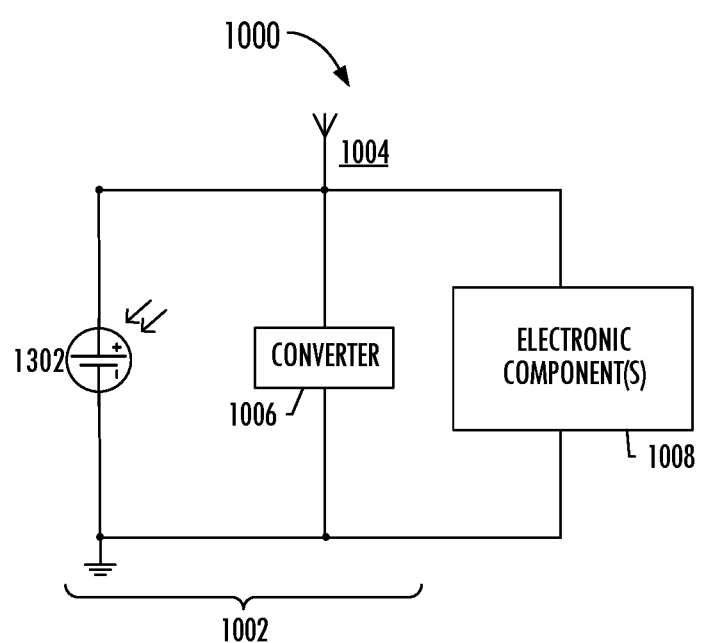

FIGS. 11, 12 and 13 more particularly illustrate additional configurations of power harvesting circuitry 1002 according to example implementations of the present disclosure. As shown in FIG. 11, the at least one electronic component 1008 may include a power source 1102 connected to an electrical load 1104. The power source may correspond to or include functionality of power source 212, 524, 912. The electrical load may include one or more other electronic components such as those that correspond to or include functionality of control component 208, 522, 908, flow sensor 210, 520, input device 910, heating element(s) 220, 532, 732, or piezoelectric/piezomagnetic mesh of nozzle 920, or the like. Again, other suitable electronic components include an accelerometer, gyroscope, proximity sensor, display, and the like.

As shown in FIG. 11, the power harvesting circuitry 1002 may he configured to harvest power to charge the power source 1102, and the power source may in turn provide power to the electrical load 1104. In some implementations, the power harvested by the power harvesting circuitry may power the electrical load independent of, or in conjunction with the power source. Thus, in some of these examples, the power harvesting circuitry may he configured to harvest power from the RF energy to charge the power source, and the power source may be configured to power at least one other electronic component such a control component, flow sensor, input device, aerosol production component, sensor, display, or the like.

As shown in FIG. 12, in some example implementations, the power harvesting circuitry 1002 further includes an accumulator 1202. In these example implementations, the power harvesting circuitry may be configured to harvest power from the energy to charge the accumulator that is configured to power or charge the at least one electronic component 1008. The accumulator may be or include a suitable energy storage component such as a rechargeable lithium-ion battery, rechargeable thin film solid-state battery, rechargeable supercapacitor or the like. In some examples, the converter 1006 may be configured to convert RF energy to DC power and store the power in the accumulator until a charge threshold of the accumulator is achieved. In instances in which the charge threshold of the accumulator has been achieved, the accumulator may be configured to boost an output voltage level thereof, using a direct current (DC) voltage boost converter circuitry. The voltage output may be disabled upon the charge declining below the charge threshold.

In some examples, the power harvesting circuitry 1002 may include a number of other electronic components, such as amplifiers, analog-to-digital (ADC) converters, digital-to-analog (DAC) converters, resistors, indicators and the like to form the electrical circuit. As shown in FIG. 12, in some examples, the accumulator 1202 may be configured to discharge power through an operational amplifier 1204 (e.g., inverting or non-inverting operational amplifier) in which the operational amplifier may be configured to amplify and regulate a discharge current from the accumulator to the at least one electronic component 1008. The power harvesting circuitry may also include a variable resistor 1206 in which the accumulator may be configured to discharge current through the resistor to the at least one electronic component. The resistor may have a variable resistance and thereby the current may have variable amperage that effects a variable wattage. For example, the resistor may be or include a three-terminal resistor such as a potentiometer. As such, the resistor may be configured to adjust a voltage or current range of the power being discharged from the accumulator to the at least one electronic component. In some examples, an output voltage of the accumulator may be set to 3.3 volts, and the voltage may be adjustable from 1.8 volts up to 5.25 volts using the variable resistor.

The power harvesting circuitry 1002 may also include an indicator 1208 (e.g., LED, quantum dot-based LED, organic LED) configured to visually indicate a voltage level of the accumulator 1202. In some examples, the indicator may be coupled to a control component such as one that may be or include the functionality of control component 208, 522, 908. In these examples, the power harvesting circuitry may generate and transmit a signal to the control component for driving the indicator in which the signal may correspond to a voltage level of the accumulator.

As shown in FIG. 13, in some examples, the power harvesting circuitry 1002 may further include a photovoltaic cell 1302 configured to harvest power from light energy. In these examples, the at least one electronic component 1008 may be powered or charged from either the converter 1006 or the photovoltaic cell, or switchably from both the converter and photovoltaic cell. In some example implementations, the at least one electronic component may be configured to receive power from the converter, and switch to the photovoltaic cell only after the converter has discharged by at least a threshold amount.

Figure 14:
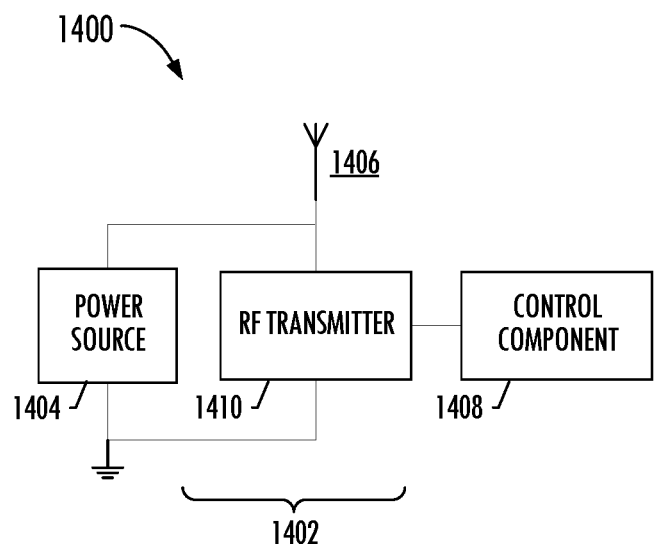
Figure 15:
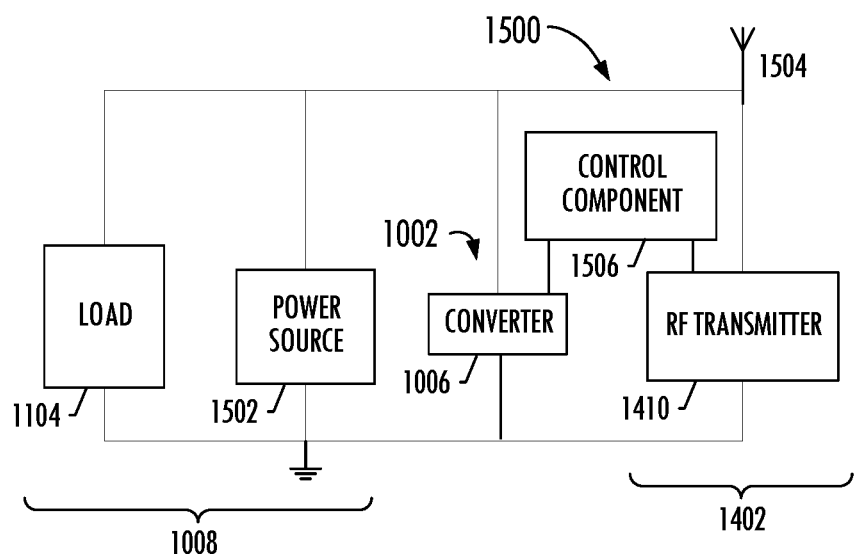

FIG. 14 illustrates another circuit diagram of circuitry 1400 that may be implemented on and/or incorporate functionality of any one or more of aerosol delivery devices 100, 300, 700, and 800 according to various example implementations of the present disclosure. In some more particular examples, the circuit diagram is of circuitry that may be implemented on and/or incorporate functionality of any one or more of control body 102, 302, 702 or 802. Additionally or alternatively, in some examples, the circuit diagram is of circuitry that may be implemented on and/or incorporate functionality of a cartridge of an aerosol delivery device, such as cartridge 104, 804.

As shown in FIG. 14, in some examples, the circuitry 1400 includes power transmission circuitry 1402 for transmitting power as RF energy to one or more other aerosol delivery devices according to example implementations of the present disclosure. The power transmission circuitry may include or be operatively connected to a power source 1404 to acquire electrical power that is converted through the operation of the power transmission circuitry into RF energy for transmission. The power transmission circuitry may also include or be otherwise operatively connected to an antenna 1406 configured to transmit the RF energy developed by the power transmission circuity. The power transmission circuitry may also be operatively connected to a control component 1408 configured to regulate or otherwise control operation of the power transmission circuitry. The power source may correspond to or include functionality of power source 212, 524, 912, and the control component may correspond to or include functionality of control component 208, 522, 908, or the like.

As shown in FIG. 14, the power transmission circuitry 1402 may be configured to transmit RF energy that can be received by one or more other devices. For example, the power transmission circuitry may transmit RE energy to devices that are instances of or otherwise incorporate example implementations of the aerosol delivery device 1000, or any other device that incorporates power harvesting circuitry, such as power harvesting circuitry 1002, for example.

As shown in FIG. 14, the power transmission circuitry 1402 may be configured to convert power stored in the power source 1404 into RF energy within a frequency range of 800 to 1000 megahertz (MHz) and transmit the RF energy away from the aerosol delivery device 1400.

As shown in FIG. 14, the power transmission circuitry 1402 may include an RE transmitter 1410. In some example implementations, the RF transmitter is operatively connected to the power source 1404 such that the RF transmitter receives electrical energy from the power source. The RF transmitter may then boost, condition, or otherwise convert the electrical energy received from the power source to be in a form and magnitude that can be to be transmitted into an area surrounding the circuitry 1400. For example, circuitry suitable for power boosting and/or conversion and other battery management operations, such as the BQ25504 device available from Texas Instruments, may be used in some example implementations of the power transmission circuitry. In some example implementations, the RF transmitter may also include voltage monitoring circuitry configured to evaluate and measure the voltage available for transmission via the RF transmitter and the antenna 1406. In some example implementations, the RF transmitter may incorporate an analog-to-digital converter, such as an ADS62PXX device from Texas instruments, provide additional conditioning of the electrical energy provided to the RF transmitter.

As shown in FIG. 14, the RF transmitter 1410 is configured to modulate the electrical energy received from the power source 1404, and supplies RF energy to the antenna 1406, to transmit the RE energy. The operation of one or more of aspects of the power transmission circuitry 1402 may be controlled by the control component 1408 to implement one or more protocols associated with the transmission of RE energy from the circuitry 1400. The control component 1408 may directly interact with one or more other components within the power transmission circuitry 1402 to selectively activate or deactivate such components, such as through the application of control signals to one or more integrated circuits configured to receive such control signals. In some example implementations, the control component may selectively activate or deactivate switches (such as relays, p-channel mosfet devices, n-channel mosfet devices, or the like, for example) to disrupt or establish connections between and among components in the power transmission circuity.

Some example implementations of the aerosol delivery devices, control bodies, and cartridges herein include power harvesting circuity configured to receive RF energy from an external RF source and harvest power from the RF energy to charge a rechargeable power source and also include power transmission circuitry operatively coupled to the power source and configured to convert electrical energy drawn from the power source to RF energy and transmit the RF energy. As such, example implementations of the aerosol delivery devices, control bodies, and cartridges described and otherwise disclosed herein overcome and address many of the technical challenges that arise in contexts and situations where multiple devices seek to access and harvest power from RF energy.

FIG. 15 illustrates a circuit diagram of circuitry 1500 that may be implemented with and/or incorporate functionality of circuitry 1000 and 1400, according to various example implementations of the present disclosure. As shown in FIG. 15, in some examples, the circuitry 1500 includes both power harvesting circuitry 1002 and power transmission circuitry 1402. As described above, the power harvesting circuitry, may include the converter 1006 and the load 1104, As also described above, the power transmission circuitry may also include the RF transmitter 1410. As shown in FIG. 15, the power harvesting circuitry and the power transmission circuitry are both operatively coupled to the power source 1502, the antenna 1504, and the control component 1506. As such, the control component may be used to selectively activate and deactivate the power harvesting circuitry and/or selectively activate and deactivate the power transmission circuitry to allow an aerosol delivery device equipped with the circuitry to both harvest power from received RF energy and transmit RF energy, and to control one or more interactions between the power source, the power harvesting circuitry, and the power transmission circuitry. The power source may correspond to or include functionality of power source 212, 524, 912, 1102 or the like, and the control component may correspond to or include functionality of control component 208, 522, 908, 1408 or the like.

Many of the technical challenges associated with RF energy transmission and the use of power harvesting in portable electronic devices are rooted in the limited range of conventional base stations or similar devices used to supply RF energy for harvesting. Since the energy available for harvesting from an RF signal decreases significantly with distance, users of devices that can use power harvesting technology are often restricted to a relatively confined geographic area when seeking to recharge their device, or may experience poor harvesting performance when moving into, out of, and through the area covered by a particular transmission.

Some example implementation of the aerosol delivery devices, control bodies, and cartridges described and otherwise disclosed herein address these and other technical challenges by using the power harvesting circuitry and power transmission circuitry included in such example implementations to establish a mesh network or other network topology to transmit RF energy suitable for power harvesting over a geographic area that can extend beyond the range of a single RF energy source.

FIG. 16 illustrates an example network 1600 according to example implementations of the present disclosure. As shown in FIG. 16, the network 1600 includes a base station 1602 which transmits RF energy over a limited geographic range. The network 1600 also includes aerosol delivery devices 1604, 1606, 1608, 1610, and 1612, each of which are disposed at different positions within a geographic area. It will be appreciated that any implementation of the circuitry 1500 consistent with this disclosure may be used in example implementations of the aerosol delivery devices 1604, 1606, 1608, 1610, and 1612.

In some example implementations, the aerosol delivery devices 1604, 1606, 1608,1610, and 1612 establish a mesh network or other similar network to transmit RF energy beyond the geographic range limits associated with the base station 1602. In the example shown in FIG. 16, aerosol deliver devices 1604 and 1606, receive RF energy directly from the RF base station 1602, as they are within range of the base station. As shown in FIG. 16, the aerosol delivery devices 1608 and 1610 are outside the range of the base station 1602, but are sufficiently close to aerosol delivery devices 1604 and 1606, and are able to receive RF energy from aerosol delivery devices 1604 and 1606, and harvest power from the received RF energy. In the example shown in FIG. 16, each of aerosol delivery devices 1604, 1606, 1608, and 1610 are able to transmit RF energy that is received by aerosol delivery device 1612, which in turn harvests power from the RF energy.

In some example implementations, the aerosol delivery devices 1604, 1606, 1608, 1610, and 1612 act as network nodes to route RF energy across the network established by the aerosol delivery devices and the base station 1602. In some example implementations, the various aerosol delivery devices may connect directly, dynamically, and non-hierarchically to as many nodes as possible. As such, the power harvesting circuity in some example implementations of the aerosol delivery devices, control bodies, or cartridges described or otherwise disclosed herein may be configured to receive RF energy from a plurality of RF sources, that are disposed within a mesh network architecture, and the power transmission circuity in some example implementations of the aerosol delivery devices, control bodies, or cartridges described or otherwise disclosed herein may be configured to transmit RF energy to one or more remote aerosol delivery devices that are disposed within a mesh network architecture.

In other example implementations additional network protocols, rules, user preferences, or other limitations may be imposed on the operation of one or more delivery devices within a given network. Regardless of the network topology within which a given aerosol delivery device, control body, or cartridge may operate, circuitry, such as the control component 1506 and/or other circuitry may control the operation of the power harvesting and power transmission circuity. For example, in some example implementations where a single antenna, such as antenna 1504, is used to both transmit and receive RF energy, the control component is configured to selectively activate and deactivate the power harvesting circuity and selectively activate and deactivate the power transmission circuitry.

The selective activation and deactivation of the power harvesting circuitry and the power transmission circuitry may be used, regardless of the configuration of one or more antennas, to implement or reflect any of a number of protocols, rules, user preferences, or the like. For example, circuitry, such as the control component 1506 or the like, may be configured to selectively activate and deactivate the power harvesting circuity and selectively activate and deactivate the power transmission circuitry based on a charging status of the rechargeable power source. For example, in situations where the battery or other rechargeable power source 1502 in an implementation of circuitry 1500 is at a low level or otherwise under a predetermined threshold, the control component 1506 may deactivate the power transmission circuitry 1402 until the power source achieves a charging level above the threshold.

FIG. 17 depicts an example flowchart illustrating a decision flow 1700 that may be used by a control component, such as control component 1506 for example, according to example implementations. As shown in FIG. 17, the decision flow first includes deciding, at block 1702, whether the battery or other rechargeable power source, such as the battery or other rechargeable power source 1502 in an implementation of circuitry 1500, is at a low level or otherwise under a predetermined threshold. If the battery or other rechargeable power source is not below the predetermined threshold, the decision flow transitions to block 1704, where the control component allows the relevant power transmission circuitry, such as power transmission circuitry 1402 for example, to continue its normal operation. The decision flow then transitions back to the start of the decision flow repeats. If the battery or other rechargeable power source was found at block 1702 to be under the predetermined threshold, the decision flow transitions to block 1706, where the power transmission circuitry is deactivated. The decision flow transitions back to the start of the decision flow, and the power transmission circuitry remains deactivated until the battery or other rechargeable power source is no longer below the relevant threshold.

In some example implementations, circuitry, such as the control component 1506 or the like, is configured to selectively activate and deactivate the power harvesting circuity or selectively activate and deactivate the power transmission circuitry based at least in part on a distance between an aerosol delivery device and a remote aerosol delivery device. If, for example, circuitry 1500 determined that it was too far from another aerosol delivery device (such as by detecting RF energy at a very low level, for example) the control component 1506 may deactivate the power transmission circuity 1402 to avoid a situation where the circuitry would lose power and be unlikely to reliably recharge. In another example, the control component may activate power harvesting circuitry in situations where one or more other devices are detected at close range.

In some example implementations, circuitry, such as the control component 1506 or the like, may be configured to selectively activate and deactivate the power harvesting circuity and selectively activate and deactivate the power transmission circuitry based on a user input. For example, a user may choose not to participate in a given network, and may interact with the control component and/or other processing circuitry via a user interface to indicate whether or not the power harvesting circuitry 1002 or power transmission circuitry 1402 should be activated.

In some example implementations, circuitry, such as the control component 1506 or the like, may be configured to selectively activate and deactivate the power harvesting circuity and selectively activate and deactivate the power transmission circuitry based on the use of the aerosol delivery device. For example, the control component may deactivate the power harvesting circuity 1002 and the power transmission circuitry 1402 when a flow of air is detected through a portion of a relevant aerosol delivery device housing. Deactivating the power harvesting circuity and the power transmission circuitry when an aerosol delivery device is in use may ensure that power is properly delivered to the heater or other aerosol production component.

In some example implementations, circuitry, such as the control component 1506 or the like, may interact with the power harvesting circuity 1002 and the power transmission circuitry 1402 to implement a trusted device protocol, where the transmission of RF energy or the harvesting of power from RF transmissions is only performed in connection with a trusted device, for example. In some example implementations, the power harvesting circuitry and the power transmission circuitry may be permitted to operate only in certain contexts, such as those involving devices from a particular manufacturer, known-compatible charging systems, or previously identified, specific users. In some example implementations involving specifically identified users, the user of a particular device may update and/or maintain a list of trusted users and/or associated user device identifications on the user's aerosol delivery device. In another example, an aerosol delivery device may communicate with (e.g., paired via Bluetooth) with the user's mobile computing device and may leverage a trusted list maintained thereon (e.g., in form of phone directory, address book, social networking service, dedicated app for aerosol delivery device that includes trusted list, or the like to obtain a list of friends or other contacts and determine if a device within range and/or a device requesting to share power (and/or a user of that device) is in the trusted list.

FIG. 18 depicts an example flowchart illustrating a decision flow 1800 that may be used by a control component, such as control component 1506 for example, in connection with a trusted-user protocol according to example implementations. As shown in FIG. 18, the decision flow first includes receiving, at block 1802, a request from a remote device to engage in power sharing with the receiving aerosol delivery device. The decision flow then transitions to block 1804, where the control component determines whether the request was received from a trusted user or trusted source. As discussed or otherwise disclosed herein, a list of trusted users and/or devices may be maintained locally on a given aerosol delivery device, or stored remotely on one or more systems accessible by the aerosol delivery device. If the request is determined to be received from a trusted user or source, the decision flow transitions to block 1806, where the request is accepted, and the relevant power transmission and power harvesting circuitry are selectively activated to allow for power sharing with the requesting device. If the request is determined to be received from a user or device that is not on a relevant trusted user list, the decision flow transitions to block 1808, where the request is denied and the relevant power harvesting and power transmission circuitry are selectively deactivated.

In some example implementations involving a trusted-user protocol, the power harvesting circuity 1002 and the power transmission circuitry 1402 may be configured to operate in connection with a unique crystal that operates at a particular frequency. This frequency can serve as a type of device identification or device signature unique to a given aerosol delivery device. When one aerosol delivery device engages in a handshaking operation with another aerosol delivery device to begin a transmission or other operation within a network, the user may decide whether to accept a given connection, either manually or automatically by checking the frequency or other device identifier against a list of trusted users.

Since some example implementations described or otherwise disclosed herein involve multiple aerosol delivery devices operating as nodes in a network, additional data may be transferred among and between aerosol delivery devices in connection with the transmission of RF energy. For example, one or more software updates, informational notices, social media information, or other data may be exchanged at the time a given aerosol delivery device joins a network or as part of the transmission and receipt of RF energy within a given network.

In some example implementations involving a base station that may be in a fixed location and otherwise supplies RF energy (such as RF base station 1602, for example), the base station may also be configured as a policy beacon to provide an indication regarding whether or not the use of an aerosol delivery device is permitted in a certain location. In some example implementations, the policy information may be incorporated into the RF energy broadcast for power harvesting, and demodulated from the RF energy upon receipt by an aerosol delivery device. In some example implementations, the base station may be configured to broadcast the policy information at another frequency, or via another protocol (such as TDMA, for example) so as not to mix the policy information signals with the RE energy intended to be used for power harvesting. In some example implementations, the base station may periodically segment its broadcast, such that policy information is shared at periodic intervals, followed by a resumption of the transmission of RF energy for harvesting.

FIG. 19 illustrates various operations in a method 1900 for controlling an aerosol delivery device according to example implementations of the present disclosure. The aerosol delivery device may include a control body coupled or coupleable with a cartridge to form the aerosol delivery device. The cartridge may be equipped with a heating element configured to activate and vaporize components of an aerosol precursor composition. The method may comprise receiving RF energy from an external RE transmitter via an antenna, as shown at block 1902. The method may also comprise harvesting power from the RF energy, using a converter, for powering or charging a at least one electronic component, as shown at block 1904. The method may also comprise converting electrical energy drawn from a power source to RF energy and transmitting the RF energy via an antenna, as shown at block 1906.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-19 or as otherwise described above may be included in an aerosol delivery device according to the present disclosure.

Many modifications and other implementations of the disclosure will come to mind to one skilled in the art to which this disclosure pertains having the benefit of the teachings presented in the foregoing descriptions and the associated figures. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol delivery device comprising:
 a housing structured to retain an aerosol precursor composition;
 an aerosol production component configured to produce an aerosol from the aerosol precursor composition;
 power harvesting circuitry configured to receive radio-frequency (RF) energy from an external RF source and harvest power from the RF energy to charge a rechargeable power source; and
 power transmission circuity operatively coupled to the power source and configured to convert electrical energy drawn from the power source to RF energy and transmit the RF energy.

2. The aerosol delivery device of claim 1, wherein the power harvesting circuitry is further configured to receive RF energy from a plurality of RF sources, the plurality of RF sources disposed within a mesh network architecture.

3. The aerosol delivery device of claim 1, wherein the power transmission circuitry is further configured to transmit RF energy to a remote aerosol delivery device disposed within a mesh network architecture.

4. The aerosol delivery device of claim 1, further comprising an antenna operatively coupled to the power harvesting circuitry and the power transmission circuitry, the antenna configured to receive and transmit RF energy.

5. The aerosol delivery device of claim 1, comprising processing circuitry contained within the housing, the processing circuitry configured to selectively activate or deactivate the power harvesting circuitry and selectively activate or deactivate the power transmission circuitry.

6. The aerosol delivery device of claim 5, wherein the processing circuitry is configured to selectively activate or deactivate the power harvesting circuitry or the power transmission circuitry based on a charging status of the rechargeable power source.

7. The aerosol delivery device of claim 5, wherein the processing circuitry is configured to selectively activate or deactivate the power harvesting circuitry or the power transmission circuitry based at least in part on a distance between the aerosol delivery device and a remote aerosol delivery device.

8. The aerosol delivery device of claim 5, wherein the processing circuitry is configured to selectively deactivate the power harvesting circuitry in response to a user input.

9. The aerosol delivery device of claim 5, wherein the processing circuitry is configured to selectively deactivate the power harvesting circuitry in response to a flow of air through at least a portion of the housing.

10. The aerosol delivery device of claim 5, wherein the processing circuitry is configured to selectively deactivate the power transmission circuitry in response to a user input.

11. The aerosol delivery device of claim 5, wherein the processing circuitry is configured to selectively deactivate the power transmission circuitry in response to a flow of air through at least a portion of the housing.

12. The aerosol delivery device of claim 1, comprising processing circuitry contained within the housing, wherein the processing circuitry is configured to selectively activate or deactivate the power harvesting circuitry or the power transmission circuitry based on a determination of whether a remote aerosol delivery device is identified on a list of trusted devices.

13. A control body coupled or coupleable with a cartridge to form an aerosol delivery device, the cartridge containing an aerosol precursor composition and an aerosol production component configured to produce an aerosol from the aerosol precursor composition, the control body comprising:
power harvesting circuitry configured to receive radio-frequency (RF) energy from an external RF source and harvest power from the RF energy to charge a rechargeable power source; and
power transmission circuity operatively coupled to the power source and configured to convert electrical energy drawn from the power source to RF energy and transmit the RF energy.

14. The control body of claim 13, wherein the power harvesting circuitry is further configured to receive RF energy from a plurality of RF sources, the plurality of RF sources disposed within a mesh network architecture.

15. The control body of claim 13, wherein the power transmission circuitry is further configured to transmit RF energy to a remote aerosol delivery device disposed within a mesh network architecture.

16. The control body of claim 13, further comprising an antenna operatively coupled to the power harvesting circuitry and the power transmission circuitry, the antenna configured to receive and transmit RF energy.

17. The control body of claim 13, further comprising processing circuitry configured to selectively activate or deactivate the power harvesting circuitry or selectively activate or deactivate the power transmission circuitry.

18. The control body of claim 17, wherein the processing circuitry is configured to selectively activate and deactivate the power harvesting circuitry and the power transmission circuitry based on a charging status of the rechargeable power source.

19. The control body of claim 17, wherein the processing circuitry is configured to selectively activate and deactivate the power harvesting circuitry and the power transmission circuitry based at least in part on a distance between the aerosol delivery device and a remote aerosol delivery device.

20. The control body of claim 17, wherein the processing circuitry is configured to selectively deactivate the power harvesting circuitry in response to a user input.

21. The control body of claim 17, wherein the processing circuitry is configured to selectively deactivate the power harvesting circuitry in response to a flow of air through at least a portion of the housing.

22. The control body of claim 17, wherein the processing circuitry is configured to selectively deactivate the power transmission circuitry in response to a user input.

23. The control body of claim 17, wherein the processing circuitry is configured to selectively deactivate the power transmission circuitry in response to a flow of air through at least a portion of the housing.

24. The control body of claim 13, comprising processing circuitry configured to selectively activate or deactivate the power harvesting circuitry or the power transmission circuitry based at least in part on a determination of whether a remote aerosol delivery device is identified on a list of trusted devices.

25. A system for operating aerosol delivery devices in a mesh network architecture, the system comprising:
a plurality of aerosol delivery devices comprising respective power harvesting circuitry and respective power transmission circuitry,
wherein the respective the power harvesting circuitry of an aerosol delivery device in the plurality of aerosol delivery devices is configured to receive radio frequency (RF) energy from the respective power transmission circuitry of another aerosol delivery device in the plurality of aerosol delivery devices that is configured to transmit the RF energy.

* * * * *